United States Patent
Jugl et al.

(10) Patent No.: US 11,872,381 B2
(45) Date of Patent: Jan. 16, 2024

(54) DRIVE TRAIN FOR DIAL OF A TORSION-SPRING ASSISTED WIND-UP INJECTION DEVICE

(71) Applicant: SANOFI, Paris (FR)

(72) Inventors: Michael Jugl, Frankfurt am Main (DE); Stefan Blancke, Frankfurt am Main (DE); Axel Teucher, Frankfurt am Main (DE); Ralph Donald Quentin Collings, Bristol Bristol (GB); James Robert Coop, Bristol Bristol (GB); James Anthony West, Bristol Bristol (GB); Stephen Francis Gilmore, Bristol Bristol (GB); Daniel David Higgins, Bristol Bristol (GB); Mark Digby Teucher, Bristol Bristol (GB); Anthony Paul Morris, Warwick (GB); Matthew Meredith Jones, Warwick (GB); William Geoffrey Arthur Marsh, Warwick (GB); Samuel Keir Steel, Warwick (GB)

(73) Assignee: Sanofi, Paris (FR)

( * ) Notice: Subject to any disclaimer, the term of this patent is extended or adjusted under 35 U.S.C. 154(b) by 1115 days.

(21) Appl. No.: 16/479,790

(22) PCT Filed: Jan. 22, 2018

(86) PCT No.: PCT/EP2018/051374
§ 371 (c)(1),
(2) Date: Jul. 22, 2019

(87) PCT Pub. No.: WO2018/134385
PCT Pub. Date: Jul. 26, 2018

(65) Prior Publication Data
US 2020/0345945 A1   Nov. 5, 2020

(30) Foreign Application Priority Data

Jan. 23, 2017 (EP) .................................. 17305065
Sep. 19, 2017 (EP) .................................. 17306212

(51) Int. Cl.
*A61M 5/315* (2006.01)
*A61M 5/31* (2006.01)

(52) U.S. Cl.
CPC .... *A61M 5/31585* (2013.01); *A61M 5/31526* (2013.01); *A61M 5/31553* (2013.01);
(Continued)

(58) Field of Classification Search
CPC ................ A61M 5/20; A61M 5/31553; A61M 5/31526; A61M 5/31585; A61M 5/31541;
(Continued)

(56) References Cited

U.S. PATENT DOCUMENTS

2013/0131602 A1   5/2013  Kemp et al.
2014/0350478 A1*  11/2014  Hansen ............. A61M 5/31593
                                                      604/207
(Continued)

FOREIGN PATENT DOCUMENTS

CN      103998077       8/2014
CN      104768597       7/2015
(Continued)

OTHER PUBLICATIONS

International Preliminary Report on Patentability in International Application No. PCT/EP2018/051374, dated Jul. 23, 2019, 8 pages.
(Continued)

*Primary Examiner* — Emily L Schmidt
*Assistant Examiner* — Alexandra Lalonde
(74) *Attorney, Agent, or Firm* — Fish & Richardson P.C.

(57) ABSTRACT

A drive train for a wind-up injection device is described. The drive train includes a torsional energy storage adapted to be
(Continued)

loaded or unloaded by a rotatable element, a rotatable user handle, a rotationally driveable expelling mechanism adapted to expel the liquid drug, and a clutch element coupled with the torsional energy storage via the rotatable element and including a ratchet for maintaining the rotatable element at one of a number of discrete angular positions against the torque of the torsional energy storage. The clutch element is adapted to transmit the torque from the user handle to the torsional energy storage, or alternatively from the torsional energy storage to the expelling mechanism. The ratchet is switchable from one position to an adjacent position by a torque transmitted from the user handle to the torsional energy storage. The drive train is adapted to dampen torque peaks visco-elastically and/or visco-frictionally.

8 Claims, 13 Drawing Sheets

(52) U.S. Cl.
CPC ............... *A61M 2005/3143* (2013.01); *A61M 2205/0216* (2013.01)

(58) Field of Classification Search
CPC .............. A61M 5/3157; A61M 5/2033; A61M 5/31501; A61M 5/31528; A61M 5/31533; A61M 5/31545; A61M 5/31548; A61M 5/31551; A61M 5/3156; A61M 5/3158; A61M 2205/0216; A61M 2005/3143; A61M 2005/2086; A61M 2005/2418; A61M 2005/202; A61M 2005/3151
See application file for complete search history.

(56) References Cited

U.S. PATENT DOCUMENTS

| | | |
|---|---|---|
| 2015/0148750 A1 | 5/2015 | Pedersen et al. |
| 2016/0008549 A1* | 1/2016 | Plumptre ............ A61M 5/5086 604/111 |
| 2018/0161507 A1 | 6/2018 | Fabien et al. |
| 2018/0200446 A1* | 7/2018 | Grimoldby ....... A61M 5/31591 |

FOREIGN PATENT DOCUMENTS

| | | |
|---|---|---|
| CN | 104781869 | 7/2015 |
| JP | 2015-503377 | 2/2015 |
| JP | 2015-517856 | 6/2015 |
| JP | 2015-533321 | 11/2015 |
| JP | 2016-509900 | 4/2016 |
| WO | WO 2010/022810 | 3/2010 |
| WO | WO 2013/098194 | 7/2013 |
| WO | WO 2013/178372 | 12/2013 |
| WO | WO 2014/056868 | 4/2014 |
| WO | WO 2014/072298 | 5/2014 |
| WO | WO 2014/139916 | 9/2014 |
| WO | WO 15/132234 | 9/2015 |
| WO | WO 2015/145294 | 10/2015 |
| WO | WO 2016/055628 | 4/2016 |
| WO | WO 2016/193620 | 12/2016 |

OTHER PUBLICATIONS

International Search Report and Written Opinion in International Application No. PCT/EP2018/051374, dated Apr. 19, 2018, 11 pages.

* cited by examiner

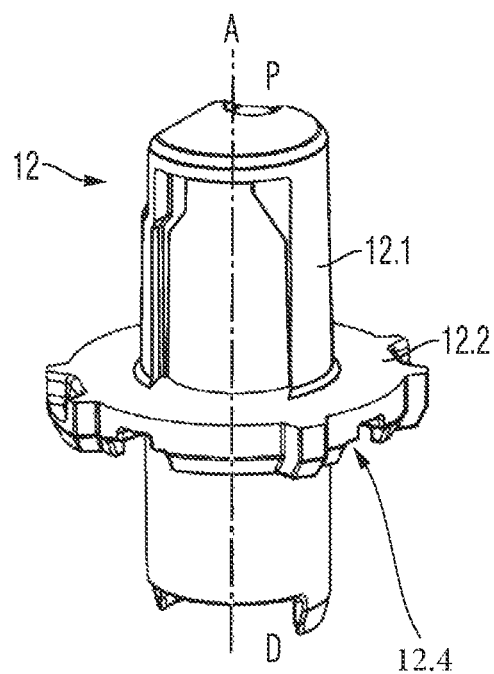
Fig. 3
Prior art
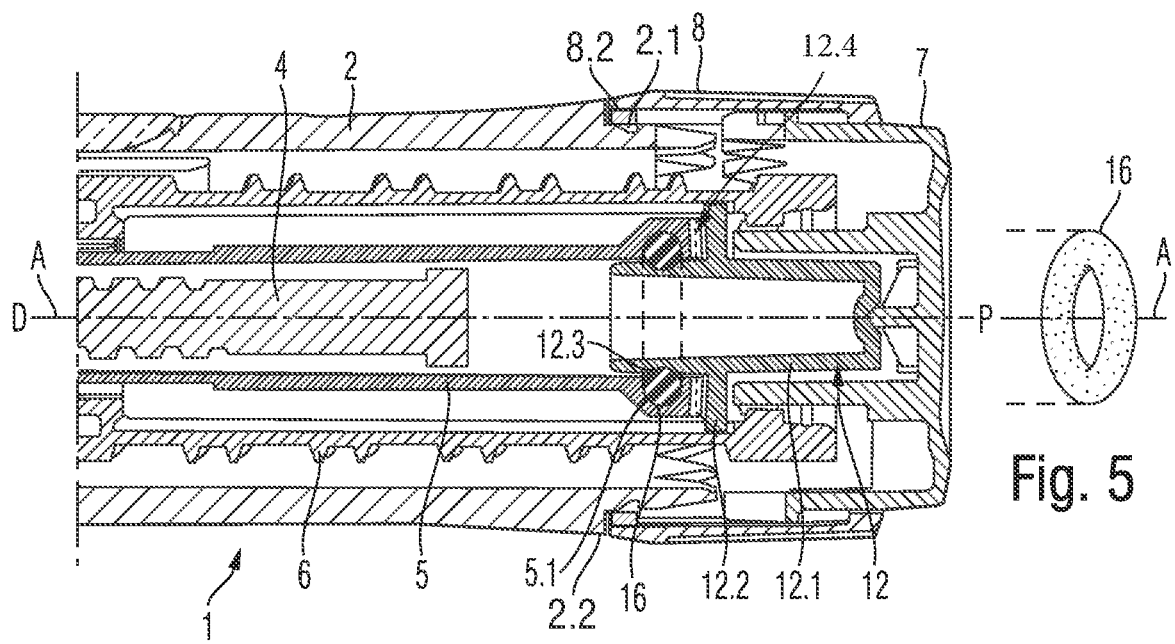
Fig. 4
Fig. 5

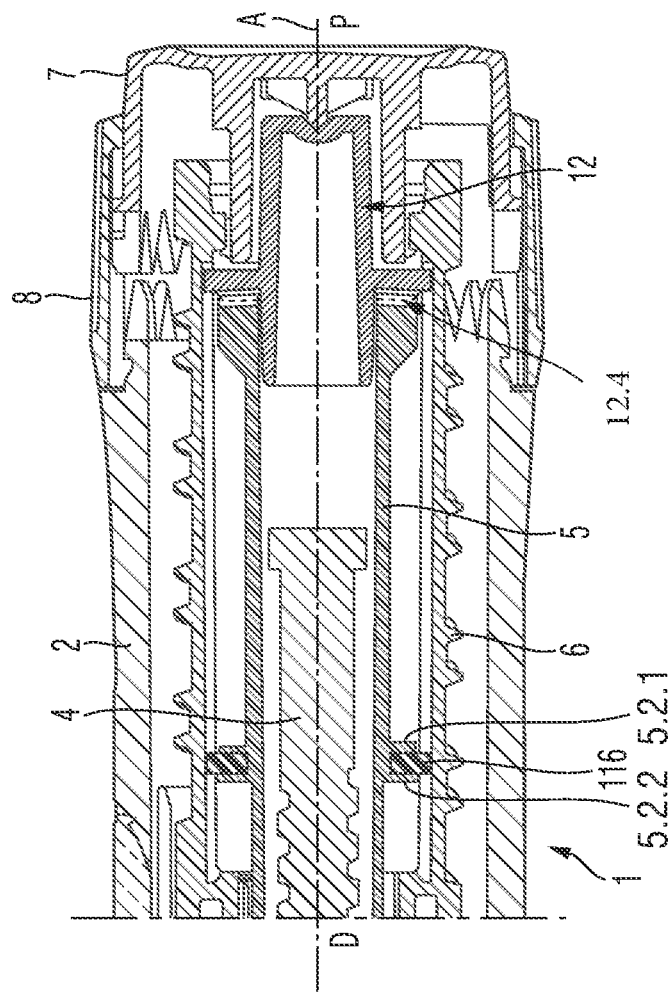
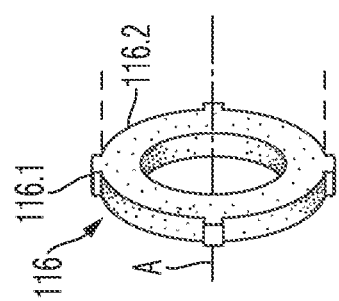
Fig. 6
Fig. 7

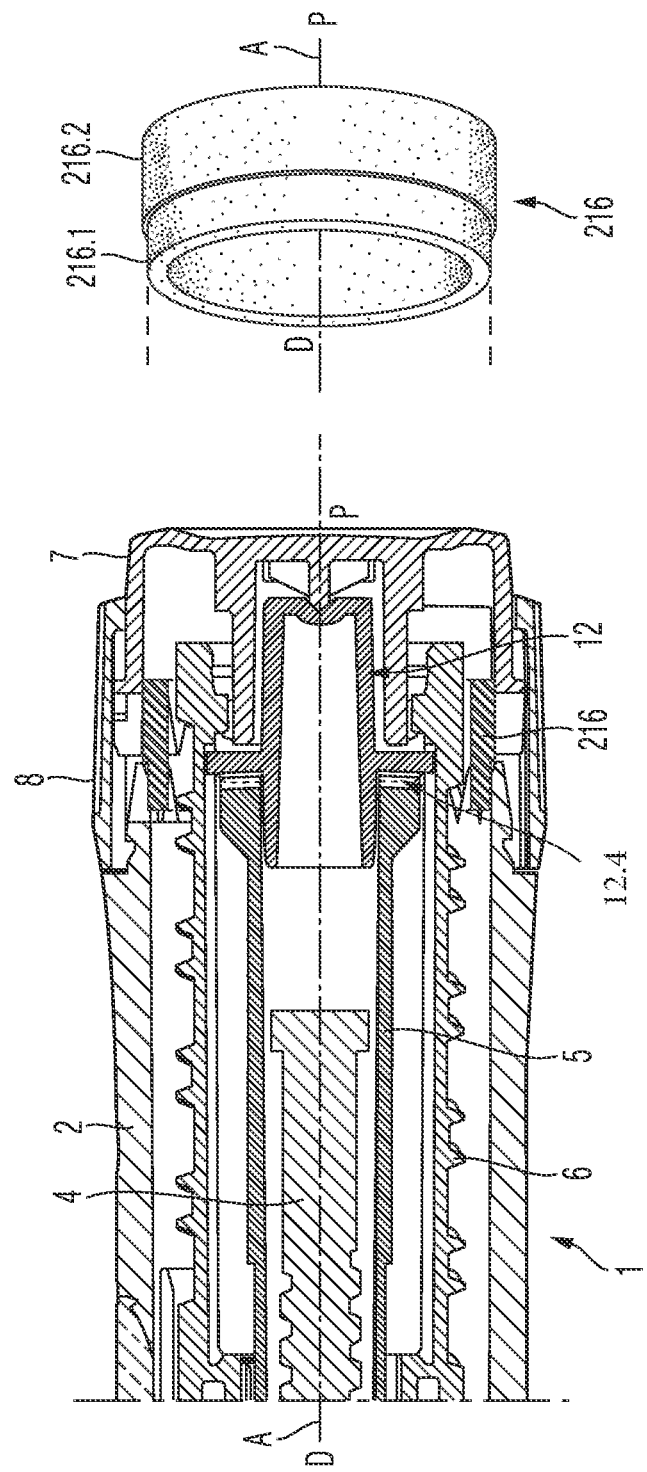

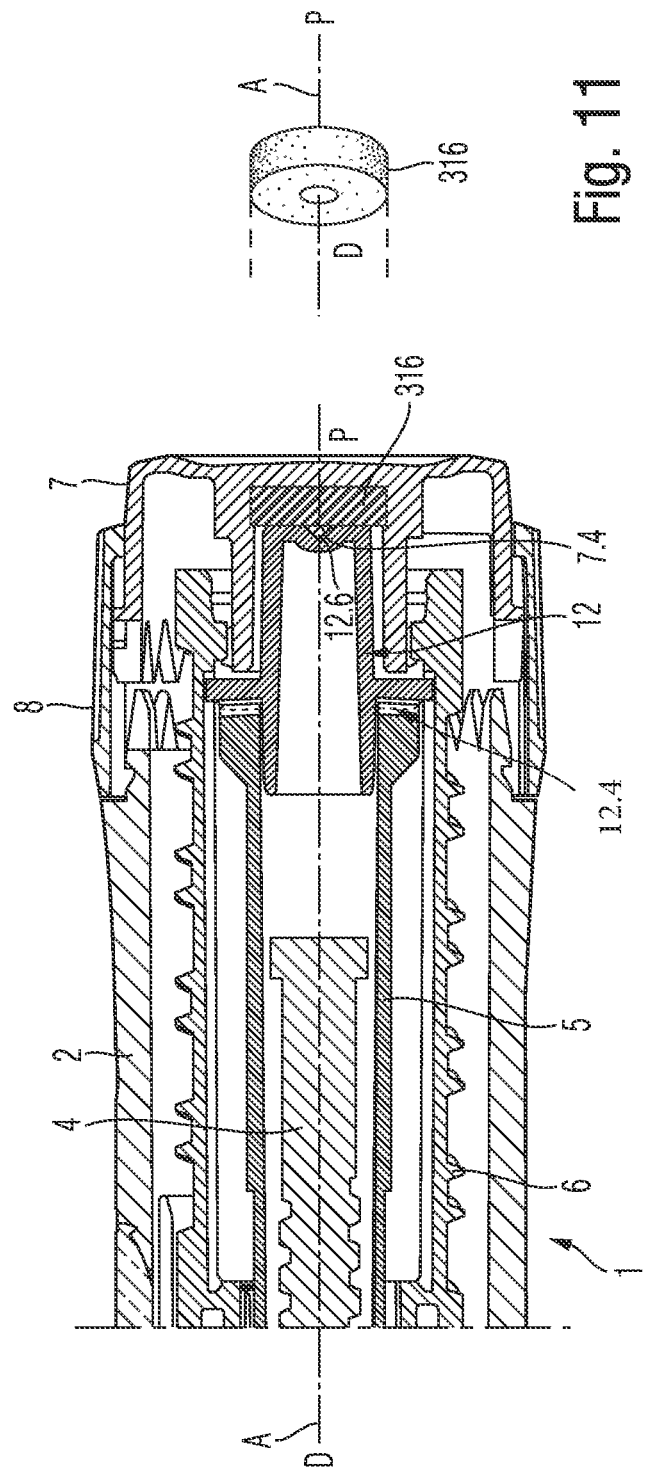

(A-A)

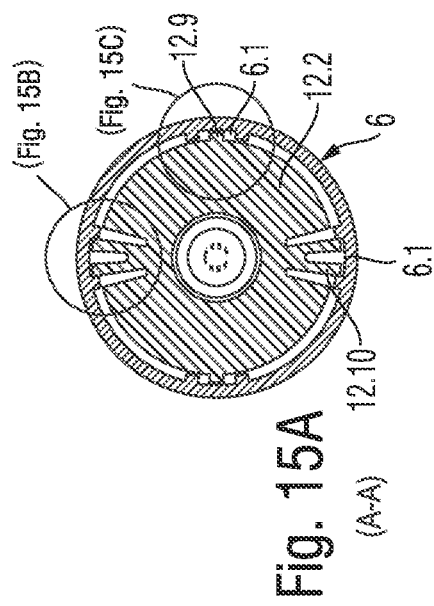
Fig. 15A (A-A)
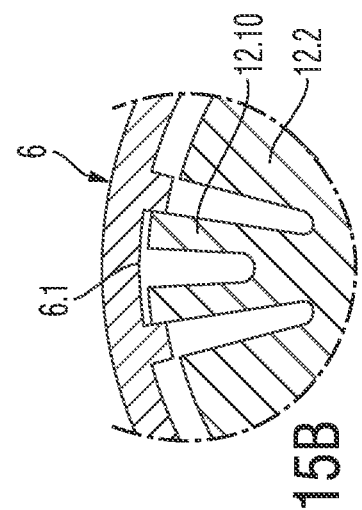
Fig. 15B
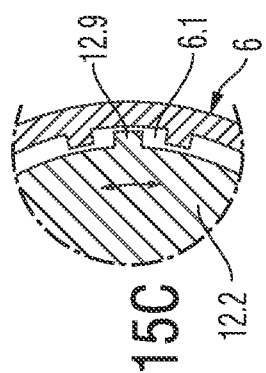
Fig. 15C
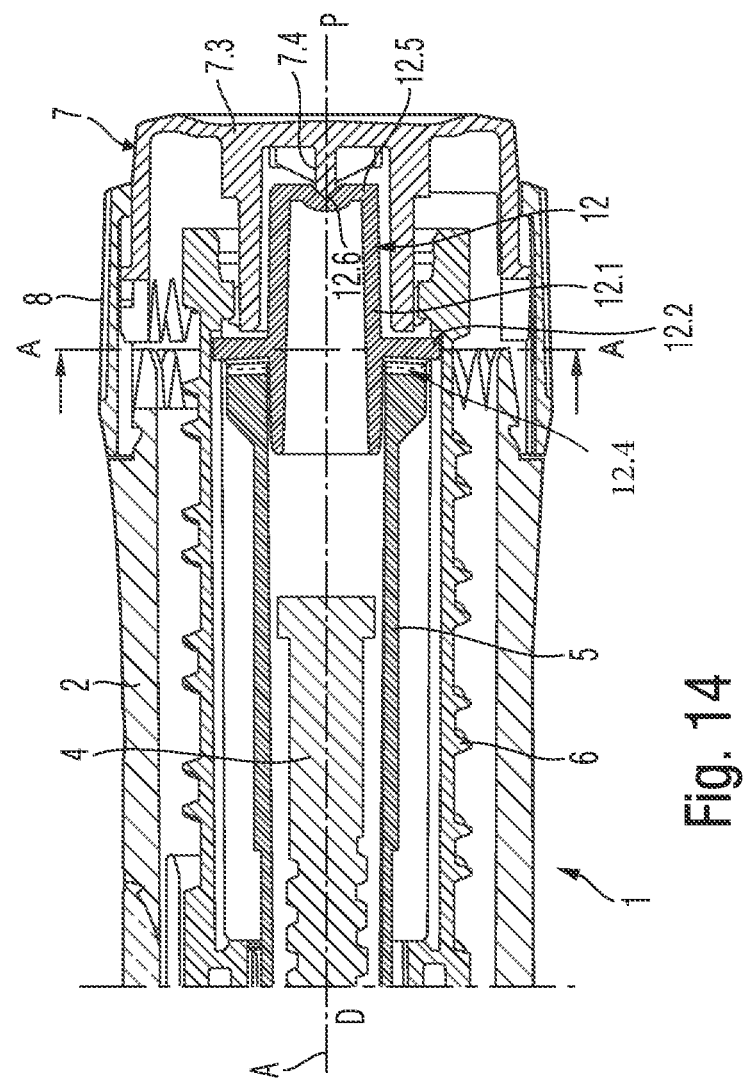
Fig. 14

DRIVE TRAIN FOR DIAL OF A TORSION-SPRING ASSISTED WIND-UP INJECTION DEVICE

CROSS REFERENCE TO RELATED APPLICATIONS

The present application is the national stage entry of International Patent Application No. PCT/EP2018/051374, filed on Jan. 22, 2018, which claims priority to European Patent Application No. 17305065.9, filed on Jan. 23, 2017, and European Patent Application No. 17306212.6, filed on Sep. 19, 2017, the disclosures of which are incorporated herein by reference.

TECHNICAL FIELD

The disclosure generally relates to a dial mechanism for a torsion-spring assisted wind-up injection device.

BACKGROUND

From the state of the art, wind-up injection devices are known where a torque applied by the user upon a user handle such as a rotatable dial grip is transferred along a drive train to wind up and/or wind down a rotational energy storage unit such as a torsion spring. The rotational energy storage unit drives a rotationally drivable expelling mechanism. When the rotational energy storage is released, a drug dose corresponding to the accumulated rotational energy is delivered.

It is further known that the drive train may comprise a ratchet for maintaining a rotatable element at one of a number of discrete angular positions against the torque load of the rotational storage unit, whereby the ratchet is switchable from one position to an adjacent position by application of a torque to the user handle.

A dial-up/dial-down mechanism for a wind-up injection device for setting or reducing a dose by rotating a dose setting member in a first or in a second direction is described in document WO 2013/098194 A2. The dial-up/dial-down mechanism operates a torsion spring which is strained when setting a dose and unstrained when rotating the dose setting element in the second direction. In order to secure the torsion spring when strained, a ratchet arm following the rotation of the dose setting element in the first direction, engages a toothed element such that engagement of the at least one ratchet arm with teeth of the toothed element prevents unwinding of the torsion spring, and wherein the rotation of the dose setting member in the first direction moves the ratchet arm from one tooth to the subsequent tooth of the toothed element, and rotation of the dose setting member in the second direction lowering the set dose activates the ratchet arm to disengage the teeth of the toothed element and thereby allow the torsion spring to move the ratchet arm in the second direction to the previous tooth such that the force accumulated in the torsion spring reduces incrementally. In order to provide a smooth movement when dialling down the set dose, the at least one ratchet arm is associated with friction means dampening the movement of the ratchet arm by the torsion spring.

The document WO 2010/022810 describes a medicament injection device, wherein a cartridge with a septum and a needle unit having front and rear needles are configured for relative movement from a state where the septum is sealed to a state where the septum is pierced by the rear needle. The injection device may include a needle shield and be configured for piercing the septum by the rear needle when the front needle is operated relative to the needle shield. The injection device may also include a damping mechanism configured for limiting the speed of movement of the cartridge relative to the needle unit. The injection device may also include an indicator generating a signal when a piston driver has travelled the complete stroke length, wherein the indicator has a deflection element that is deflected prior to or during movement of the cartridge relative to the housing.

The document WO 15132234 describes a device for delivery of medicament that has an elongated housing, a container mounted within the housing and adapted to contain liquid medicament, a stopper slidably arranged within said container, and a delivery mechanism comprising a resilient member, a plunger assembly having one end connected to the stopper and a second end being operably connected to the resilient member, a rotatable latch for releasably retaining the plunger assembly in a first position where the resilient member has an accumulated energy, where rotation of the latch releases the plunger assembly such that the accumulated energy is transferred to the plunger assembly for driving the stopper within the container whereby the medicament within said container is delivered to an injection site. After delivery of the medicament a rotator having a hard stop feature aligns with a rib on the protective shield to prevent retraction of the protective shield.

SUMMARY

An object of the present disclosure is to provide a drive train for a wind-up injection device driven by a torsional energy storage with a smoothened rotational dialling and with an improved maintaining of a dialled dose. A further object of the present disclosure is to provide a wind-up injection device with such a drive train. A further object of the present disclosure is to provide a process for manufacturing such a drive train.

With respect to the drive train, the object is achieved by a drive train according to claim 1. With respect to the wind-up injection device, the object is achieved by a wind-up injection device according to claim 26.

Exemplary embodiments are provided in the dependent claims.

According to the disclosure, a drive train for a wind-up injection device for injecting a liquid drug comprises a torsional energy storage adapted to be loaded or unloaded by a rotatable element, a rotatable user handle, a rotationally driveable expelling mechanism adapted to expel the liquid drug and a clutch element. The clutch element is coupled with the torsional energy storage via the rotatable element and comprises a ratchet for maintaining the rotatable element at one of a number of discrete angular positions against the torque of the torsional energy storage. The clutch element is adapted to transmit a torque from the user handle via the rotatable element to the torsional energy storage or alternatively from the torsional energy storage via the rotatable element to the expelling mechanism. The ratchet is switchable from one position to an adjacent position by a torque transmitted from the user handle to the torsional energy storage. The drive train is adapted to dampen torque peaks visco-elastically and/or visco-frictionally. Thereby, the user experiences a smoother handling of the wind-up injection device.

In an embodiment of the disclosure, a drive train comprises a visco-elastic dampening element that is adapted to elastically transmit a torque. It is an advantage of this embodiment that a visco-elastic dampening element is inexpensive and easy to integrate in a drive train according to the state of the art.

In an embodiment of the disclosure, a drive train comprises a visco-frictional dampening element that is adapted to frictionally resist a rotation. It is an advantage of this embodiment that a visco-frictional dampening element is inexpensive and easy to integrate in a drive train according to the state of the art.

In an embodiment of the disclosure, a drive train comprises a visco-frictional dampening element that is arranged between two elements of the drive train that are rotatable relative to each other. Thereby, torque peaks and torque minima that occur when the torsional energy storage is wind up via the ratchet are dampened.

In an embodiment of the disclosure, a drive train comprises a visco-frictional dampening element with at least one surface of elastic rubber adapted to slide along a contact surface of an element of the drive train when rotated relatively to that element. Such a surface of elastic rubber is easy to manufacture and provides a reliable visco-frictional dampening.

In an embodiment of the disclosure, a drive train comprises a visco-elastic dampening element that is arranged between the user handle and the ratchet.

In an embodiment of the disclosure, the torsional energy storage comprises a housing with a longitudinal axis extending from a proximal towards a distal end and a torsional drive spring with a distal spring end non-rotatably engaged to the housing and with a proximal spring end torsionally tensible around the longitudinal axis relative to the housing. The expelling mechanism comprises a drive sleeve arranged within the housing and rotatable around the longitudinal axis, wherein rotation relative to the housing causes a piston rod to translate relative to the housing. The clutch element comprises a cylindrical clutch section and is adapted to releasably non-rotatably couple the proximal spring end of the drive spring with the drive sleeve.

In an embodiment of the disclosure, the drive train comprises a visco-frictional dampening element that is adapted to frictionally resist a rotation of the clutch element relative to the drive sleeve around the longitudinal axis, wherein a proximal portion of the drive sleeve is adapted to receive a distal portion of the cylindrical clutch section coaxially to the longitudinal axis and wherein the visco-frictional dampening element is arranged between inner surface of the proximal portion of the drive sleeve and the outer surface of the distal portion of the cylindrical clutch section and is adapted to frictionally engage an inner surface of the drive sleeve. The visco-frictional dampening element increases the frictional resistance that the user must overcome to turn the dose selector. Thereby, the relative difference between torque peaks and torque minima caused by the ratchet is reduced or dampened.

In an embodiment of the disclosure, the drive train comprises a visco-frictional dampening element which is received in a toric space formed by a first circumferential recess provided in the cylindrical clutch section and an radially adjacent second circumferential recess provided in the inner surface of the drive sleeve. A radially inwardly directed face of the dampening element frictionally engages the cylindrical clutch section. A radially outwardly directed face of the visco-frictional dampening element frictionally engages the drive sleeve.

In an embodiment of the disclosure, the drive train comprises a visco-frictional dampening element which is an O-ring. As an advantage, an O-ring is inexpensive, available in various sizes and easy to assemble in a drive train.

In an embodiment of the disclosure, the drive train comprises a drive sleeve that is arranged within the number sleeve and rotatable around the longitudinal axis, wherein rotation relative to the housing causes a piston rod to translate relative to the housing, wherein the dampening element is coaxially arranged between the outer surface of the drive sleeve and the inner surface of the number sleeve and wherein the dampening element is adapted to frictionally resist a rotation of the drive sleeve relative to the number sleeve.

In an embodiment of the disclosure, the dampening element is formed as a dampening ring with radial protrusions circumferentially arranged in equal angular steps, wherein the inner diameter of the dampening ring is adapted to abut the outer diameter of the drive sleeve and wherein the radially outward faces of the radial protrusions are adapted to abut the inner diameter of the number sleeve. The dampening ring provides a frictional resistance against a rotation of the number sleeve relative to the drive sleeve when setting the dose. By such an increased friction, torque peaks along the drive train that cause acoustic and tactile discontinuities, are reduced.

In an embodiment of the disclosure, a pair of radially protruding drive sleeve rings is formed on the outer surface of the drive sleeve, wherein a proximal drive sleeve ring abuts the dampening element in a proximal direction and a distal drive sleeve ring abuts the dampening element in a distal direction.

In an embodiment of the disclosure, a button with at least one tubular button wall closed by a button lid on its proximal end is non-rotatably coupled with the user handle, wherein the dampening element is formed as a visco-frictional dampening element arranged to frictionally resist a rotation of the button relative to the housing.

In an embodiment of the disclosure, the housing provides a tubular inner surface at least partly along the longitudinal axis, wherein the visco-frictional dampening element is formed as a tubular dampening element with a tapered end circumferentially frictionally engaging the tubular inner surface of the housing and with an expanded end circumferentially frictionally engaging an inner surface of the at least one tubular button wall.

In an embodiment of the disclosure, the clutch element provides a clutch lid on the proximal end of the cylindrical clutch section, wherein the clutch lid is received in the at least one tubular wall of the button and wherein the visco-frictional dampening element is arranged between the clutch lid and the distal face of the button lid.

In an embodiment of the disclosure, the clutch element is coupled to the rotatable element by a circumferentially resilient visco-elastic dampening element.

In an embodiment of the disclosure, the rotatable element is formed as a tubular number sleeve adapted to at least partially receive the clutch element, wherein the visco-elastic dampening element radially protrudes from the clutch element and is received with its radially outward end circumferentially non-slippably in an axial slot that is arranged on the inner surface of the tubular number sleeve coaxially to the longitudinal axis.

In an embodiment of the disclosure, the visco-elastic dampening element is formed as at least one resilient arm.

In an embodiment of the disclosure, the visco-elastic dampening element is formed as at least one resilient fork.

In an embodiment of the disclosure, the clutch element comprises at least one radially protruding radial stop with a radially outward end received in an axial slot with circumferential slip.

In an embodiment of the disclosure, the user handle provides at least one pocket and is releasably non-rotatably coupled with the rotatable element by a button providing at least one driving clip, wherein a driving clip is led axially displaceable along the longitudinal axis in a corresponding pocket and is wedged non-rotatably when urged in a proximal direction relative to the pocket.

In an embodiment of the disclosure, the at least one driving clip and the corresponding pocket are tapered towards a proximal end.

In an embodiment of the disclosure, the user handle provides at least one pocket and is releasably non-rotatably coupled with the rotatable element by a button providing at least one driving clip, wherein a driving clip is led axially displaceable along the longitudinal axis with a rotational play in a corresponding pocket and wherein the driving clip is resiliently forced into a circumferential center position.

In an embodiment of the disclosure, proximally bifurcating resilient clip arms of a driving clip are led coaxially to the longitudinal axis in a guiding section of a corresponding pocket, wherein the resilient clip arms are bent together when abutting a proximally tapered holding section of the pocket.

In an embodiment of the disclosure, a driving clip with a proximally tapered conical tip is arranged longitudinally displaceable and with a rotational play along a guiding section of a corresponding pocket, wherein a proximal holding section of the pocket is form-fittingly tapered to the conical tip and wherein the button is urged in a proximal direction relative to the user handle by a spring.

In an embodiment of the disclosure, the user handle is releasably non-rotatably coupled with the rotatable element by a button, wherein the button provides a rotational play relative to the user handle and wherein a visco-frictional dampening element is arranged to frictionally resist a rotation of the button relative to the user handle.

In an embodiment of the disclosure, the user handle provides at least one pocket adapted to receive a driving clip of a button with a rotational play.

In an embodiment of the disclosure, a visco-frictional layer is arranged between a proximally facing front surface of the driving clip and an opposing distally facing front surface of the pocket.

In an embodiment of the disclosure, a visco-frictional layer is arranged between a radially outwardly facing radial surface of the driving clip and an opposing radially inwardly facing radial surface of the pocket.

In an embodiment of the disclosure, the torsional energy storage comprises a torsional spring formed as a spiral spring or as a helical spring.

In an embodiment of the disclosure, the torsional energy storage comprises a compression spring and a gear element adapted to transform a translation into a rotation, wherein the translational side of the gear element is coupled to the compression spring and wherein the rotational side of the gear element is coupled to the clutch element.

In an embodiment of the disclosure the drive train comprises a visco-frictional dampening element that is adapted to frictionally resist a rotation, wherein the visco-frictional dampening element is formed as a bushing that is torque proof coupled with the user handle. The bushing is also longitudinally coupled with the user handle and with the housing. A surface of the bushing at least partially visco-frictionally engages the outer surface of the housing.

The bushing according to this embodiment advantageously guides the user handle and simultaneously, by its visco-frictional engagement, dampens torque peaks along the drive train from the user handle towards the torsional energy storage, thus providing a smoother user experience. Furthermore, the holding torque required from the clutch element and its ratchet can be reduced. Furthermore, said visco-frictional engagement applied by the bushing does not reduce the torque transmitted from the torsional energy storage towards the expelling mechanism.

In an embodiment the bushing is formed as a radially inwardly protruding collar of the user handle. The surface of the collar is at least partially made of a visco-frictional material, i.e. a material that provides viscosity and friction. The collar is received in an annular recess along an outer circumference of the housing. This embodiment provides a particularly easy way of visco-frictional engaging the user handle with the housing.

In an embodiment the collar is formed radially elastically abutting the annular recess. The radial elasticity urges the surface of the collar towards the surface of the annular recess, thereby providing a reliable frictional engagement. As a further advantage, the radial play between the user handle and the housing is reduced.

In an embodiment, cut-outs longitudinally penetrate the collar, thereby improving the radial elasticity of the collar such that it is easier to mount with the housing and provides a more reliable frictional engagement.

In an embodiment of the disclosure the drive train comprises a visco-frictional dampening element that is adapted to frictionally resist a rotation, wherein the visco-frictional dampening element is arranged between the user handle and the housing. A visco-frictional dampening element according to this embodiment dampens torque peaks along the drive train from the user handle towards the torsional energy storage, thus providing a smoother user experience. Furthermore, the holding torque required from the clutch element and its ratchet can be reduced. Furthermore, said visco-frictional engagement applied by the bushing does not reduce the torque transmitted from the torsional energy storage towards the expelling mechanism.

In an embodiment the visco-frictional dampening element is formed as an O-ring received in an annular recess along an outer circumference of the housing and/or in an annular recess along an inner circumference of the user handle. An O-ring according to this embodiment is particularly easy to manufacture and to mount. Furthermore, if such an O-ring is made of a visco-elastic material, it reduces the radial play between the user handle and the housing.

In an embodiment of the disclosure the drive train comprises a visco-frictional dampening element that is adapted to frictionally resist a rotation, wherein the visco-frictional dampening element is torque-proof coupled to the user handle and is adapted to visco-elastically rotationally lock the user handle relative to the housing in one of a predetermined number of angular lock-in positions. Each of these angular lock-in positions coincides to one of the discrete angular positions in which the rotatable element is maintained against the torque of the torsional energy storage by the ratchet.

The torque resistance applied by the visco-elasticity of the visco-frictional dampening element in a locked-in angular position adds to the torque resistance effected by the ratchet of the clutch element. Thereby it is possible to relax the requirements regarding the ratchet. In particularity, it is possible to reduce the holding torque applied by the clutch to hold the rotatable element in one of a predetermined number of angular positions corresponding to discrete selectable dosages.

The application of the holding torque near the beginning of the drive train for loading the torsional energy storage, i.e. nearby the user handle, is advantageous in terms of a more precise tactile experience when selecting a dosage. On the other hand, the application of the holding torque near the end of the drive train, i.e. at the clutch element, is advantageous in terms of a more precise and reliable selection of the dosage itself, as tolerances along the drive train from the user handle to the clutch element do not compromise the precision of the selected dosage.

It is an advantage of this embodiment that by splitting the holding torque along the drive train, i.e. application of one part of the holding torque by the visco-elastical and visco-frictional engagement of the visco-frictional dampening element with the housing in addition to application to another part of the holding torque by the ratchet of the clutch, both the precision of the tactile experience and the precision of the set dosage can be improved.

In an embodiment, the visco-frictional dampening element is formed as at least one visco-elastical pip radially inwardly protruding along an inner circumference of the user handle. At least one radial detent is formed along an outer circumference of the housing, which is arranged concentric to said inner circumference of the user handle. The at least one radial detent is adapted to receive a pip being radially decompressed. The circumferences are radially spaced as to receive the at least one pip when radially compressed.

Thus, in a locked-in angular position where at least some of the visco-elastical pips are aligned with some of the radial detents, said pips radially decompress and effect a holding torque or resistance against a rotation off that locked-in angular position. Furthermore, in between such locked-in angular positions, visco-frictional resistance of said pips dampens torque peaks along the drive train from the user handle towards the torsional energy storage, thereby providing a smoother user experience while not compromising the efficiency of the drive train that transfers the torque from the torsional energy storage towards the expelling mechanism.

As an advantage, both the torsional dampening and the splitting of the holding torque are provided by a single element or mechanism, thereby simplifying the design and manufacturing of such a drive train.

In an embodiment, a plurality of radial detents is equidistantly formed along the outer circumference of the housing and/or a plurality of pips is equidistantly formed along the inner circumference of the user handle. With such an embodiment, a plurality of equidistant locked-in angular positions can be provided, wherein in each of these locked-in angular positions an additional holding torque is provided that, in addition to the holding torque provided by the clutch and its ratchet, holds the torsional energy storage and prevents it from dialling-down the user handle.

In an embodiment, the number of pips exceeds the number of radial detents, such that at least one visco-elastic pip is compressed between the inner circumference of the user handle and the outer circumference of the housing. Thereby, the radial play between the user handle and the housing is reduced. Furthermore, it is possible to adjust a base rotational friction that resists a rotation of the user handle relative to the housing irrespective of the angular position by means of said at least one pip being in visco-frictional engagement with the housing even in a locked-in angular position.

The disclosure further relates to a process for arranging a visco-frictional layer on a surface of the pocket and/or on a surface of the driving clip, wherein the visco-fractional layer is formed on a surface of the pocket and/or on a surface of the driving clip by multi-component injection molding. As an advantage, a cost-effective manufacturing of the drive train is possible.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein:

FIG. 3 is a perspective view of an exemplary embodiment of a clutch element of a wind-up injection device according to the state of the art, FIG. 4 is a schematic longitudinal section of a driving mechanism with an O-ring, FIG. 5 is a perspective view on a first embodiment of a dampening element formed as O-ring, FIG. 6 is a schematic longitudinal section of a driving mechanism with a distance ring, FIG. 7 is a perspective view on a distance ring, FIG. 8 is a schematic longitudinal section of a driving mechanism with a tubular dampening element, FIG. 9 is a schematic perspective view of a tubular dampening element, FIG. 10 is a schematic longitudinal section of a driving mechanism with a friction ring arranged between a clutch element and a button, FIG. 11 is a schematic perspective view of a friction ring, FIG. 14 is a schematic longitudinal section of a driving mechanism with a clutch element with resilient arms and a radial stop, FIG. 15A is schematic cross section of a clutch plate with resilient arms and a radial stop, FIG. 15B is a detail of a resilient arm, FIG. 15C is a detail of a radial stop.

Corresponding parts are marked with the same reference symbols in all figures.

DETAILED DESCRIPTION

Figure 1:
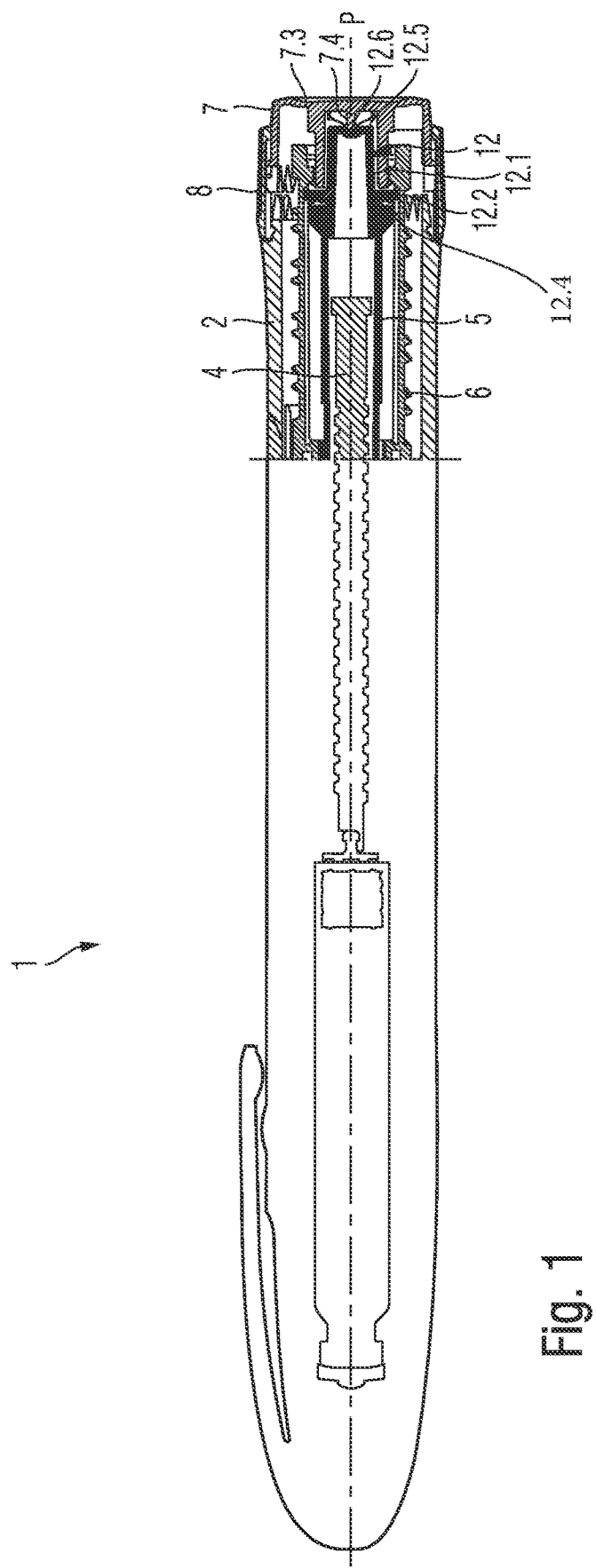
FIG. 1 is a schematic longitudinal section of an exemplary embodiment of a wind-up injection device according to prior art.

FIG. 1 shows a longitudinal section of an exemplary embodiment of a wind-up injection device 1 in the form of a wind-up injection device as known from the state of the art.

For protection of a driving function during dose setting and dose dispensing, the wind-up injection device 1 comprises at least a drive sleeve 5 adapted to move a piston rod 4 in order to dispense the dose of medicament, a drive spring 9 adapted to move the drive sleeve 5 and at least one restraining element not shown in detail adapted to partially fix the drive spring 9 against axial and rotational movement with respect to the at least one restraining element.

The wind-up injection device 1 further comprises a housing 2, a cartridge holder 3, a number sleeve 6, a button 7, a dose selector 8, a cartridge 10, a gauge element 11, a clutch element 12, a clutch spring 13 and a bearing 14. A needle assembly (not shown) comprising a needle, a needle hub and a needle cover may be provided as additional components.

The wind-up injection device 1 further comprises a longitudinal axis A extending from a proximal end P to a distal end D of the wind-up injection device 1. In the present application, the proximal direction refers to a direction that under use of the wind-up injection device 1 is located the furthest away from a drug delivery site of a patient. Correspondingly, the distal direction refers to a direction that under use of the wind-up injection device 1 is located closest to the drug delivery site of the patient. A direction perpendicular to and pointing towards the longitudinal axis A is defined as radially inwardly directed. A direction perpendicular to and pointing away from the longitudinal axis A is defined as radially outwardly directed.

The housing 2 is configured as a substantially tubular body receiving the components of the wind-up injection device 1 mentioned above. The cartridge holder 3 is arranged on a distal end of the housing 2 and attached thereto. The cartridge holder 3 receives the cartridge 10 from which a number of doses of a medicament may be dispensed by displacing a stopper 15 distally within the cartridge 10, wherein the stopper 15 is coupled to the piston rod 4. The distal end of the cartridge holder 3 may be provided with means for attaching a needle assembly (not shown), comprising a needle, a needle hub and a needle cover.

The piston rod 4 is threaded to the housing 2, wherein the piston rod 4 comprises an outer thread that engages a corresponding inner thread of the housing 2. A distal end of the piston rod 4 is engaged with the bearing 14 which acts on the stopper 15. The piston rod 4 is rotationally locked to the drive sleeve 5 such that the piston rod 4 moves axially with respect to the drive sleeve 5 when rotated.

The drive sleeve 5 has a substantially hollow cylindrical shape and encloses the piston rod 4. The drive sleeve 5 is proximally engaged to the clutch element 12 and distally engaged to the clutch spring 13. The drive sleeve 5 is further arranged within the number sleeve 6 and allowed to move distally with respect to the housing 2, the piston rod 4 and the number sleeve 6 against a bias of the clutch spring 13. The drive sleeve 5 is rotationally locked to the housing 2 during a dose setting and rotationally uncoupled from the housing 2 during dispensing a dose of medicament. Furthermore, the drive sleeve 5 is rotationally locked to the number sleeve 6 during dose dispensing.

The number sleeve 6 comprises a substantially tubular shape and is marked with a sequence of numbers on an outer circumference, which are visible through the gauge element 11. The number sleeve 6 is rotationally locked to the dose selector 8 during dose setting and thus rotated during dose setting via the dose selector 8. During dose dispensing, the number sleeve 6 is rotated together with the drive sleeve 5 by the drive spring 9. The number sleeve 8 is further axially locked to the housing 2 and rotationally coupled to the button 7 during dose setting.

The button 7 forms the proximal end of the wind-up injection device 1 and is rotatably engageable to the dose selector 8 via the clutch element 12. To activate a drug delivery mechanism, the button 7 is pressed distally as it is described further below.

The dose selector 8 is configured as a sleeve-like component with a ribbed outer surface in order to provide a grippable surface. The dose selector 8 is furthermore locked against axial movement with respect to the housing 2 and locked against rotational movement with respect to the button 7. A rotation of the dose selector 8 during dose setting charges the drive spring 9 in order to energise the drug delivery mechanism.

The drive spring 9 is inserted into the number sleeve 6, thereby enclosing a distal portion of the drive sleeve 5. The drive spring 9 comprises a distal spring end 9.1 fixed to the housing 2 and a proximal spring 9.2 end fixed to the number sleeve 6. The drive spring 9 is biased or charged during dose setting by rotating the dose selector 8 with respect to the housing 2. Because the dose selector 8 is rotationally locked to the number sleeve 6 and the number sleeve 6 is fixed to the proximal spring end of the drive spring 9, the drive spring 9 is biased and decreases its diameter approaching a torque axis as described further below.

Further components of the wind-up injection device 1 are the gauge element 11, the clutch element 12, the clutch spring 13 and the bearing 14.

The gauge element 11 comprises a generally plate- or band-like component having a central aperture (window) allowing viewing a portion of the number sleeve 6. The gauge element 11 is rotationally locked to the housing 2 but allowed to translate axially with respect to the housing 2.

The clutch element 12 is engaged to the number sleeve and rotationally locked thereto. The clutch element 12 is further locked against rotational movement to the button 7 at least during dose setting. The clutch element 12 provides an audible and/or tactile feedback for the user during dose setting and dose dispensing. The clutch element 12 may comprise a ratchet 12.4, thereby preventing the drive spring 9 from discharging via the number sleeve 6 and the drive sleeve 5.

The clutch spring 13 may be a compression spring and defines the axial position of the drive sleeve 5, the clutch element 12 and the button 7, wherein the clutch spring 13 applies a force on the drive sleeve 5 in a proximal direction.

This spring force is reacted via the drive sleeve 5, the clutch element 12 and the button 7, and further reacted by the dose selector 8 to the housing 2.

The bearing 14 is engaged to a distal end of the piston rod 4 and acts on the stopper 15 in a distal direction. The bearing 14 is axially locked and rotationally coupled to the piston rod 4.

In order to perform a drug delivery process, the wind-up injection device 1 may be operated according to the following exemplary method.

The user selects a variable dose of medicament by rotating the dose selector 8 clockwise, which generates an identical rotation of the number sleeve 6 with respect to the housing 2. A rotation of the number sleeve 6 causes the charging of the drive spring 9 as mentioned above, thereby increasing rotational energy stored within. As the number sleeve 6 rotates, the gauge element 11 translates axially due to its threaded engagement, thereby showing the value of the dialled dose.

Thus, the drive train T for charging the torsion drive spring 9 comprises the dose selector 8, the button 7, the clutch element 12 optionally comprising the ratchet 12.4 and the number sleeve 6. As the ratchet 12.4 is supported against the housing 2 via the drive sleeve 5, the drive train T also comprises the drive sleeve 5.

As a dose is set, the user may activate the drug delivery mechanism by depressing the button 7 in the distal direction, thereby initiating dose dispensation.

As a result, the button 7 and the dose selector 8 are rotationally disconnected from the number sleeve 6 and the drive spring 9. The clutch element 12 and the drive sleeve 5 move axially together with the button 7, thereby engaging the drive sleeve 5 to the number sleeve 6 such that relative rotation between the drive sleeve 5 and number sleeve 6 is prevented. Furthermore, the engagement between the housing 2 and the drive sleeve 5 releases, thus the drive sleeve 5 is allowed to rotate and is driven by the drive spring 9 via the number sleeve 6 and the clutch element 12.

Rotation of the drive sleeve 5 causes rotation of the piston rod 4 which is axially translated due to its threaded engagement to the housing 2. Rotation of the number sleeve 6 causes the gauge element 11 to move axially back into a zero position, whereby a zero dose abutment (not shown) stops the drug delivery mechanism.

Since the bearing 14 is directionally engaged with the stopper 15, the bearing 14 does not rotate when the piston rod 4 rotates. Instead, the bearing 14 is axially translated during dose dispense.

If the user releases the button 7, the clutch spring 13 returns the drive sleeve 5 to an 'at rest' position (together with the clutch element 12 and the button 7), thereby engaging the drive sleeve 5 with the housing 2, preventing further rotation and stopping dose dispense. The user may then rotate the dose selector 8, so that the number sleeve 6 returns to the zero dose abutment.

Figure 2:
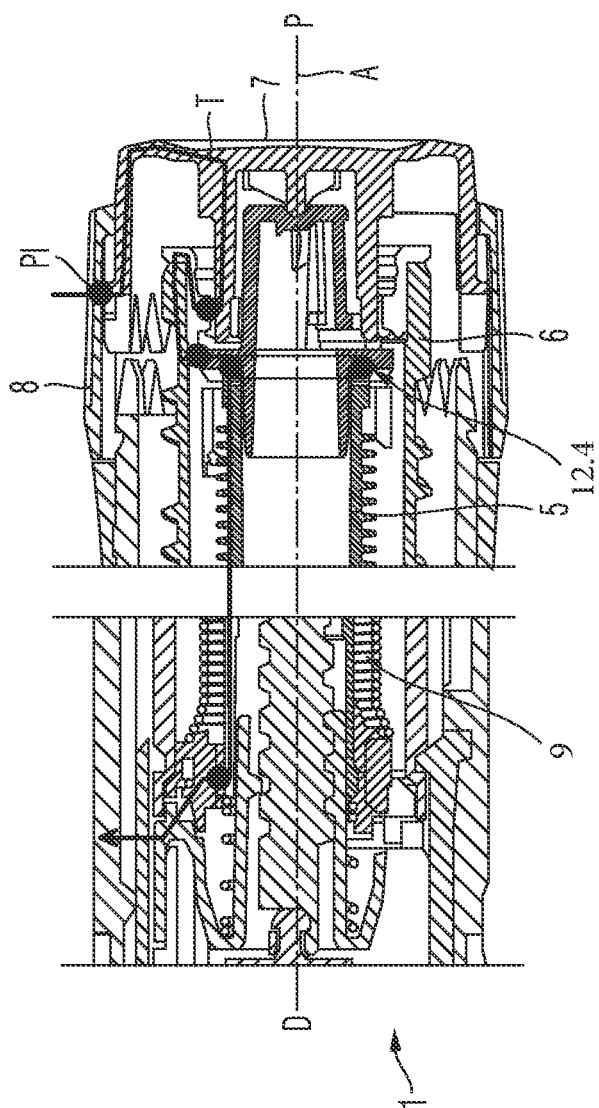
FIG. 2 is a schematic view of the drive train in a wind-up injection device according to prior art.

FIG. 2 shows a schematic view on the drive train T for loading the drive spring 9. When setting a dose, a torque is transferred from the dose selector 8 via the button 7, the number sleeve 6 onto the proximal spring end 9.2 of the drive spring 9. The dose selector 8 is longitudinally coupled with the housing 2 by means of a radially inwardly protruding collar 8.2 engaging an circumferential annular recess 2.1 arranged at a radial step or radial recess 2.2 at the proximal end of the housing 2. With the button 7 being released, i.e. in "rest" position, the ratchet 12.4 engages the drive sleeve 5 that is rotationally locked to the housing 2 such that the number sleeve 6 is held in one of a predetermined number of angular positions, thereby preventing an unloading of the drive spring 9. Along the drive train T, form-fitting or positive interfaces PI transfer the torque from the dose selector 8 onto the button 7, from the button 7 onto the number sleeve 6 and from the number sleeve 6 onto the clutch element 12.

Any of these positive interfaces PI inevitably provides a rotational play. Furthermore, due to the distance the torque is transmitted along the longitudinal axis A, torsionally weak elements such as the drive sleeve 5 may twist under torque. Beside preventing unloading of the drive spring 9, the ratchet 12.4 causes a discontinuous turning resistance when dialling a dose via the dose selector 8. Thereby, a peak torque required to step the ratchet 12.4 into the next angular position is immediately followed by a low torque. These torque discontinuities that are countered by the torque accumulated both in the drive spring 9 and in the twisted torsionally weak elements may result in an end-to-end stressing of the total rotational play over all positive interfaces PI that appears as rattling along the drive train T.

FIG. 3 shows a perspective view of an exemplary embodiment of a clutch element 12 in more detail.

The clutch element 12 comprises a substantially hollow cylindrical clutch section 12.1 a clutch plate 12.2. The clutch section 12.1 extends axially between a proximal end P and a distal end D. A distal portion of the cylindrical clutch section 12.1 extends between the distal end of the cylindrical clutch section 12.1 and the clutch plate 12.2. A proximal portion of the cylindrical clutch section 12.1 extends between the clutch plate 12.2 and the proximal end of the cylindrical clutch section 12.1.

FIG. 4 shows a schematic longitudinal section of a driving mechanism for loading the drive spring 9 with the dose selector 8 with a first embodiment of a visco-frictional dampening element 16 being arranged between the drive sleeve 5 and the clutch element 12.

The button 7 arranged at the proximal end of the wind-up injection device 1 and is formed as a double-walled tube comprising a tubular outer button wall 7.1 and a tubular inner button wall 7.2 that are coaxial to each other and with to the longitudinal axis A. The proximal front surface of the button 7 is closed by a button lid 7.3.

On the proximal end of the clutch element 12, a clutch lid 12.5 is formed closing the cylindrical clutch section 12.1. The outer or proximal surface of the clutch lid 12.5 provides a blind hole 12.6. The blind hole 12.6 is arranged centrically and is formed such that it receives a guide pin 7.4 that centrically protrudes from the button lid 7.3 in the distal direction. The clutch element 12 is forced by the clutch spring 13 in the proximal direction towards the inner or distal surface of the button lid 7.3, such that the guide pin 7.4 engages the blind hole 12.6. By their centrical arrangement, the guide pin 7.4 and the blind hole 12.6 form a bearing that hold the clutch element 12 coaxially with the longitudinal axis A.

When setting the dose via the dose selector 8, the drive sleeve 5 is rotationally locked to the housing 2 while the clutch element 12 is rotationally locked to the number sleeve 6 that is rotated to load the drive spring 9. The dampening element 16 increases the frictional resistance that the user must overcome to turn the dose selector 8. Thereby, the relative difference between torque peaks and torque minima caused by the ratchet 12.4 is reduced or dampened.

The distal end of the cylindrical clutch section 12.1 is arranged inside the proximal end of the drive sleeve 5, wherein the clutch element 12 and the drive sleeve 5 are arranged concentrically relative to each other and with respect to the longitudinal axis A. The dampening element 16 is formed as an O-ring that is shown in more detail in FIG. 5.

On the outside surface of the distal end of the cylindrical clutch section 12.1, a first circumferential recess 12.3 is formed. On the inside surface of the proximal end of the hollow drive sleeve 5 a second circumferential recess 5.1 is formed radially adjacent to the first circumferential recess 12.3. The O-ring 16 is held in the torical space formed by the radially adjacent first and second circumferential recesses 12.3, 5.1. The O-ring 16 is held such that it is in frictional engagement with the cylindrical clutch section 12.1 on a radially inwardly face and such that it is in frictional engagement with the drive sleeve 5 on a radially outwardly face. Thereby, the O-ring increases the frictional interference between the drive sleeve 5 and the clutch element 12 when the clutch element 12, rotationally locked to the number sleeve 6 rotates around the longitudinal axis A relative to the drive sleeve 5. By such an increased friction, torque peaks along the drive train T are reduced. As a further advantage, the radial play between the drive sleeve 5 and the clutch element 12 is reduced, thereby reducing unwanted rattling and tactile discontinuities that otherwise may incur upon rotation of the clutch element 12 such that the user experiences a smoothened and softer operation of the wind-up injection device 1.

FIG. 6 shows a schematic longitudinal section of a driving mechanism for loading the drive spring 9 with the dose selector 8 with a second embodiment of a visco-frictional dampening element 116 being coaxially arranged between the drive sleeve 5 and the number sleeve 6. As can be seen in more detail in FIG. 7, the dampening element 116 is formed as a distance ring 116 with four outward protrusions 116.1 that are arranged in equal-sized angular steps of 90° on the radially outwardly directed face of the ring 116 within a larger outer diameter of the distance ring 116. Along the outer circumference of the distance ring 116, radial recesses 116.2 are formed within a smaller outer diameter of the distance ring 116.

The inner diameter of the distance ring 116 fits closely to the outer diameter of the drive sleeve 5, such that frictional engagement is caused between the distance ring 116 and the drive sleeve 5. The larger outer diameter, i.e. the distance between the radial outward faces of two opposing ring protrusions 116.1, fits closely to the inner diameter of the number sleeve 6, such that frictional engagement is caused between the distance ring 116 and the number sleeve 6.

The distance ring 116 is held in its axial position along the longitudinal axis A by two drive sleeve rings 5.2.1, 5.2.2, that radially protrude outwardly from the drive sleeve 5. The distance ring 116 fits closely into the radial groove formed by the proximal drive sleeve ring 5.2.1 on its proximal side and by the distal drive sleeve ring 5.2.2 on its distal side, thereby minimizing an axial play of the distance ring 116.

The radially outward faces of the ring protrusions 116.1 frictionally engage the inner surface of the drive sleeve 6 while the radially inward face of the hole of the distance ring 116 frictionally engages the outer surface of the drive sleeve 5. When setting a dose, the drive sleeve 5 is rotationally locked relative to the housing 2. Thereby, the distance ring 116 provides a frictional resistance against a rotation of the number sleeve 6 relative to the drive sleeve 5 when setting the dose. By such an increased friction, torque peaks along the drive train T that cause acoustic and tactile discontinuities, are reduced. The distance ring 116 also supports the coaxial position of the drive sleeve 5 within the number sleeve 6, thereby reducing the radial play between the sleeves 5, 6. As an advantage, the distance ring 116 provides a smoother and softer experience to the user when dialling the dose.

Those skilled in the art will appreciate that while an arrangement of the protrusions 116.1 in equal angular steps is preferential, the number of protrusions 116.1 may vary. Number and circumferential length of the protrusions 116.1 can be chosen according to the frictional resistance that is to be achieved with the dampening element 116.

FIG. 8 shows a schematic longitudinal section of a driving mechanism for loading the drive spring 9 with the dose selector 8 with a third embodiment of a tubular visco-frictional dampening element 216 being arranged between the housing 2 and the button 7.

An essentially hollow-cylindrical tubular dampening element 216 is arranged to coaxially receive the proximal end of the number sleeve 6. The proximal end of the dampening element 216 is received in the open distal end of the button 7. As can be seen in more detail in FIG. 9, the dampening element 216 is formed rotationally symmetric around a longitudinal cylinder axis that in the mounting position coincides with the longitudinal axis A of the wind-up injection device 1. The dampening element 216 has an inside hole of a fixed diameter along the longitudinal cylinder axis, while its outside diameter steps along the longitudinal cylinder axis from a smaller first outside diameter at a tapered end 216.1 to a larger second outside diameter at an expanded end 216.2. The outside diameter at the distal tapered end 216.1 is adapted to fit the inside diameter of the proximal end of the housing 2. The outside diameter of the proximal expanded end 216.2 is adapted to fit the inside diameter of the inner button wall 7.2. It is also possible that the rotationally symmetric outside surface of the hollow-cylindrical dampening element 216 is continuously tapered, for example conically tapered, from the second larger outside diameter towards the first smaller outside diameter. The dampening element 216 is made of a flexible, elastic material with a preferably high frictional coefficient such as rubber.

In its mounting position seen in FIG. 2, the dampening element 216 is arranged coaxially to the longitudinal axis A and such that the outside surface of its tapered end 216.1 abuts the inner surface of the housing 2, while the outside surface of its expanded end 216.2 abuts the inner surface of the outer wall 7.1 of the button 7 such that the dampening element 216 is in frictional engagement with the button 7. The inside hole of the dampening element 216.1 receives the proximal end of the number sleeve 6 with the drive sleeve 5 and the clutch element 12.

The tubular visco-frictional dampening element 216 dampens, by increased frictional resistance, a rotation of the button 7 and of the dose selector 8 being rotationally coupled with the button 7 relative to the housing 2. By such an increased friction, torque peaks along the drive train T that cause acoustic and tactile discontinuities, are reduced. As a further advantage, said increased frictional resistance adds to the holding force of the clutch element 12 that prevents the drive spring from unloading. Thus, unintended unloading of the drive spring 9 is prevented more reliably. As a further advantage, said increased frictional resistance dampens rattle noises that are caused by soft torsion elements and by positive-locking interfaces along the drive train T for charging or discharging the torsion drive spring 9. As yet another advantage, the dampening element 216 does not reduce the torque exerted by the drive spring 9 on the drive sleeve 5. Therefore, the expelling of the drug by the drive sleeve 5 driving the piston rod 4 is not compromised.

FIG. 10 shows a schematic longitudinal section of a driving mechanism for loading the drive spring 9 with the dose selector 8 according to a further embodiment of a visco-frictional dampening element 316 formed as a resilient friction ring 316 being axially arranged between the proximal clutch lid 12.5 of the clutch element 12 and the distal or inner surface of the button lid 7.3.

FIG. 11 shows a more detailed perspective view of the friction ring 316, which has a centrically arranged hole adapted to receive the shaft of the guide pin 7.4 of the button 7. The thickness of the friction ring 316 along the longitudinal axis is chosen such that the friction ring 316 is compressed when the distal tip of the guide pin 7.4 is fully received in the blind hole 12.6 of the clutch element 12. The clutch element 12 is urged by the clutch spring 13 via the drive sleeve 5 axially towards the inner or distal face of the button lid 7.3, such that the friction ring 316 frictionally engages the proximal face of the clutch lid 12.5 and the distal face of the button lid 7.3, thereby causing frictional resistance against a rotation of the clutch element 12 relative to the button 7. Said increased frictional rotational resistance adds to the torque required to turn the dose selector 8 against the drive spring 9 and the ratchet 12.4 such that the relative difference between torque peaks and torque minima caused by the ratchet 12.4 is reduced or dampened. Thus, also rattle noises that are caused by soft torsion elements and by positive-locking interfaces along the drive train T for charging or discharging the torsion drive spring 9 are dampened.

Figure 13A:
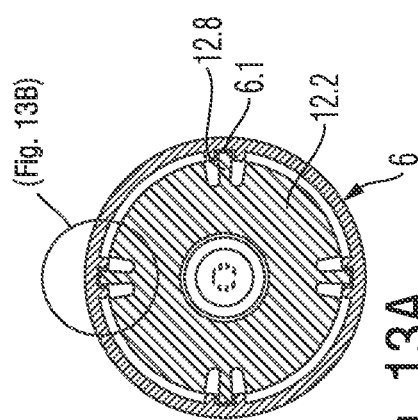
FIG. 13A is a schematic cross section of a clutch plate with resilient arms engaged in axial slots of a number sleeve.
Figure 12:
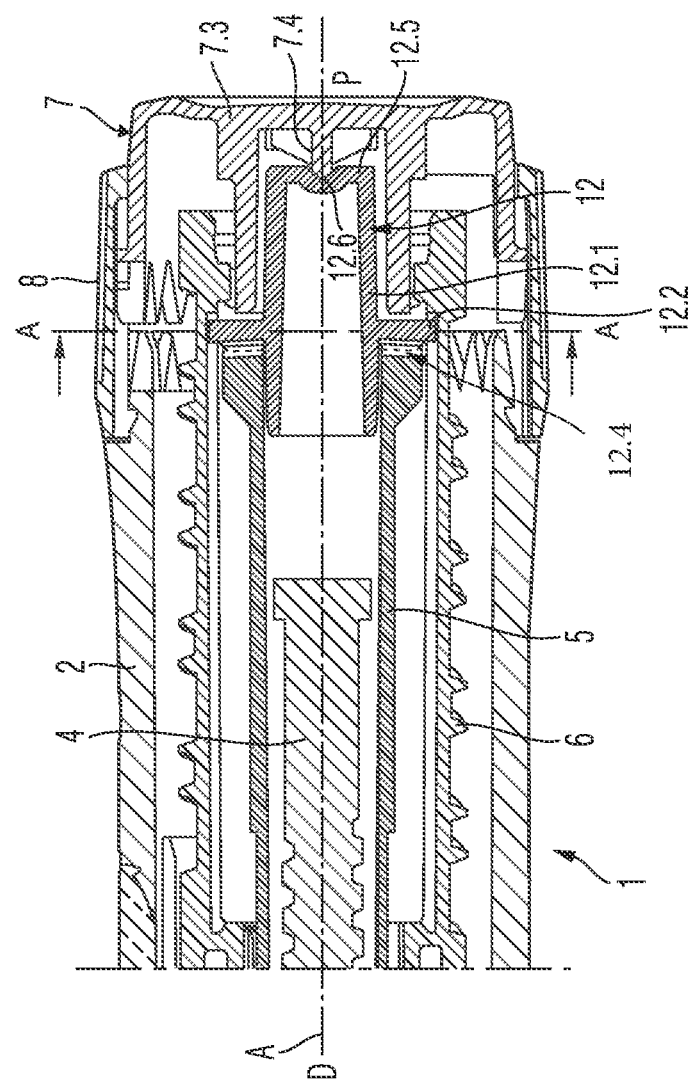
FIG. 12 is a schematic longitudinal section of a driving mechanism with a clutch element with resilient arms.

FIG. 12 shows a schematic longitudinal section of a driving mechanism located at the proximal end P of a wind-up injection device 1 according to an embodiment, wherein the clutch element 12 comprises a clutch plate 12.2 with resilient radial arms 12.8. As shown in more detail in a schematic cross section provided in FIG. 13A, the resilient arms 12.8 radially protrude over the clutch plate 12.2. Recesses 12.9 are arranged on both sides of each resilient arm 12.8 along the circumference of the clutch plate 12.2, such that the resilient arms 12.8 are bendable along the circumference of the clutch plate 12.2.

On the inner face of the number sleeve 6 axial slots 6.1 are provided that receive the radially protruding resilient arms 12.8. Each slot 6.1 is formed by a pair of axial ribs extending along the longitudinal axis A and sufficiently spaced to receive a resilient arm 12.8 with a minimal play. The resilient arms 12.8 and the corresponding slots 6.1 lock the clutch element 12 with the number sleeve 6.

Figure 13B:
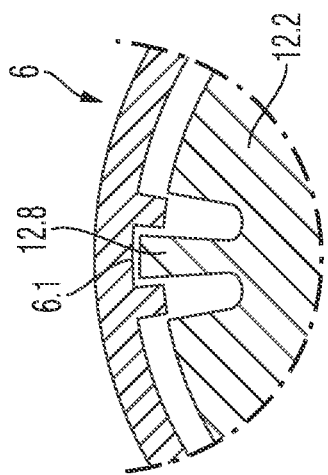
FIG. 13B is a detail of a schematic cross section of a clutch plate with resilient arms engaged in axial slots of a number sleeve.

As can be seen best in a detailed view provided in FIG. 13B, this engagement enables a limited torsion of the clutch plate 12.2 relative to the number sleeve 6, as the resilient arms 12.8 will bend under torque. Therefore, an abrupt or discontinuous rotation of the clutch element 12 relative to the number sleeve 6 will be smoothened, as peak rotational energy will be stored in, and later on released from the bended resilient arms 12.8. Thereby, this embodiment provides the user a softer handling experience of the wind-up injection device 1 and reduces rattling noises and tactile discontinuities during operation.

FIG. 14 shows a schematic longitudinal section of a driving mechanism located at the proximal end P of a wind-up injection device 1 according to an embodiment, wherein the clutch plate 12.2 comprises radial stops 12.9 in addition to resilient forks 12.10.

FIG. 15A shows a schematic cross section through the clutch plate 12 with two radially opposing resilient forks 12.10 and with two radially opposing radial stops 12.9 that are arranged in an angular offset of 90° relative to the two radially opposing resilient forks 12.10.

As can be seen best in a detailed view provided in FIG. 15B, the resilient forks 12.10 are formed with two fork arms that radially protrude over the clutch plate 12.2. The radially outward end of each resilient fork 12.10 is received in a corresponding axial slot 6.1 formed on the inner face of the number sleeve 6 by a pair of axial ribs, wherein each fork arm abuts the inner face of one of the axial ribs. The fork arms of each resilient fork 12.10 are slightly moved together as to closely fit into the axial slot 6.1.

The number sleeve 6 is engaged with the clutch element 12 by means of the resilient forks 12.10 and the corresponding axial slots 6.1 with virtually no free rotational play, whereas a limited torsion of the number sleeve 6 versus the clutch element 12 is allowed against the torque of the bending fork arms of the resilient forks 12.10. Thereby abrupt rotational movements of the clutch element 12 relative to the number sleeve 6 are smoothened, as peak rotational energy will be stored in, and later on released from the bended resilient forks 12.10. Thereby, this embodiment provides the user a softer handling experience of the wind-up injection device 1 and reduces rattling noises and tactile discontinuities during operation.

The torque-induced torsion of the clutch element 12 relative to the number sleeve 6 is limited by radial stops 12.9 that protrude from the circumference of the clutch plate 12.2 into axial slots 6.1, as shown in more detail in FIG. 15C. Thereby, the resilient forks 12.10 are protected against a torque overload.

Figure 16:
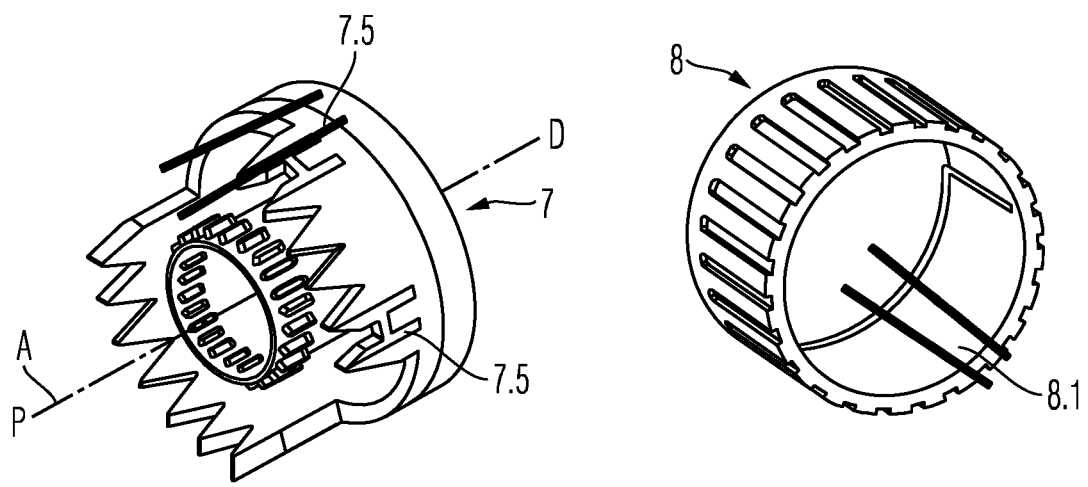
FIG. 16 is a schematic exploded view on a button with driving clips and a dose selector with pockets.

FIG. 16 shows a schematic perspective view of a button 7 and a dose selector 8. Radially protruding driving clips 7.5 are arranged on the radially outward face of the outer button wall 7.1. On the radially inward face of the dose selector 8 recess pockets 8.1 are formed that are adapted to receive corresponding driving clips 7.5 of the button 7.

When assembled, the dose selector 8 is axially locked to the housing 2, while the button 7 is urged by the clutch spring 13 via the drive sleeve 5 and the clutch element 12 in a proximal direction. Thereby, the driving clips 7.5 are led in and urged towards the proximal end of the corresponding recess pockets 8.1. The driving clips 7.5 and the recess pockets 8.1 taper towards the proximal end of the button 7 and the dose selector 8, respectively, such that the driving clips 7.5 wedge in the corresponding recess pockets 8.1. Thereby, the dose selector 8 is non-rotatably coupled with the button 7 with virtually no rotational play, such that even abrupt changes of the torque transferred from the dose selector 8 onto the button 7 and further on to the clutch element 12 will cause no or only minimal rattling noise or tactile discontinuities.

Figure 17:
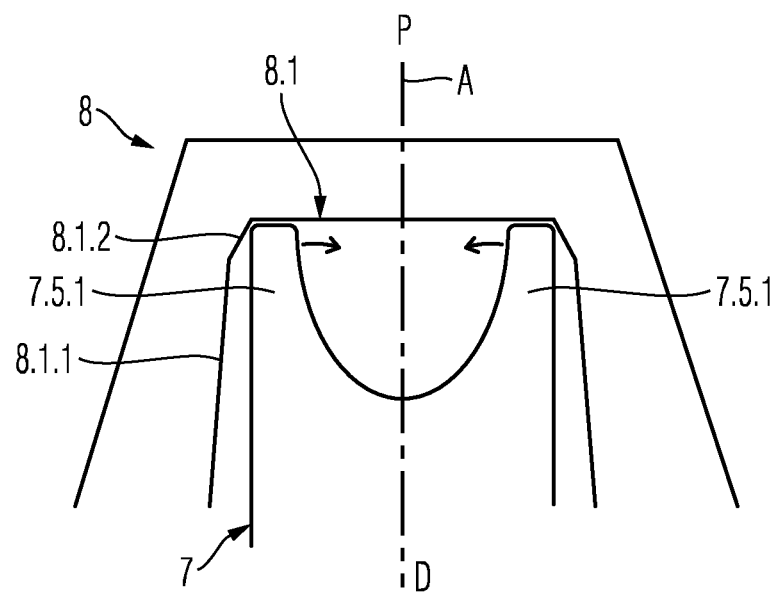
FIG. 17 is a schematic longitudinal section of a button with driving clips and a dose selector with pockets.

FIG. 17 shows a perspective view on a further embodiment of a driving clip 7.5 and a recess pocket 8.1. A driving clip 7.5 provides two clip arms 7.5.1 on its proximal end that are resilient along the circumference of the outer button wall 7.1. A recess pocket 8.1 comprises a distal guiding section 8.1.1 with a constant width and a proximal tapered or narrowing holding section 8.1.2 where the width gradually reduces. With the clip arms 7.5.1 led in the distal guiding section, a rotational play remains between the button 7 and the dosage selector 8. As the button 7 with the driving clips 7.5 is urged towards the proximal end of the dose selector 8 by the clutch spring 13, the proximal ends of the resilient clip arms 7.5.1 abut the narrowing holding section 8.1.2. Further movement in the proximal direction causes the resilient clip arms 7.5.1 of a driving clip 7.5 to bend towards each other. The restoring forces caused by the bent resilient clip arms 7.5.1 adjust the dose selector 8 in a rotational mid position relative to the button 7. If a torque is transferred from the dose selector 8 onto the button 7, the dosage selector 8 is rotationally offset from this mid position. As it is directed against the restoring forces of the resilient clip arms 7.5.1, this rotational offset absorbs part of the torque. Thereby, torque peaks along the drive train T are smoothened by the resilient clip arms 7.5.1, such that rattling noises or tactile discontinuities are minimized.

Figure 18:
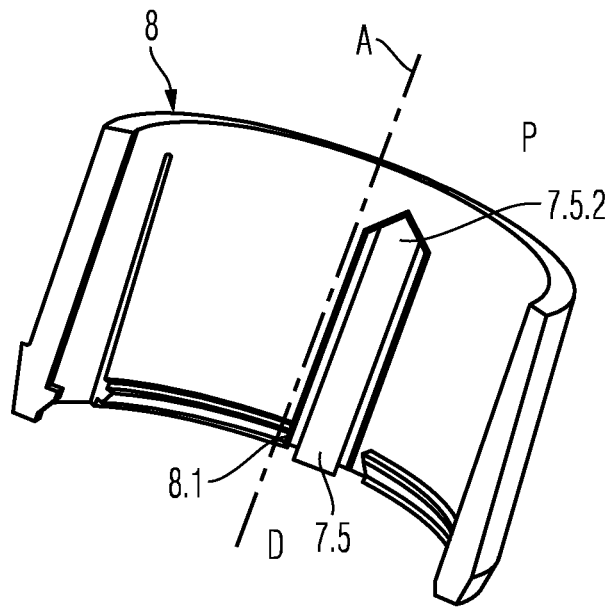
FIGS. 18, 19 are schematic perspective views on a button with driving clips and a dose selector with pockets.

FIG. 18 shows a perspective view on a further embodiment of a driving clip 7.5 and a recess pocket 8.1. A driving clip 7.5 is formed as a post with a proximal conical tip 7.5.2. The lateral or circumferential width of the pocket 8.1 exceeds the width of the clip 7.5, thereby allowing a rotational play between the button 7 and the dose selector 8. The proximal end of the recess pocket 8.1 is formed correspondingly conically to the conical tip 7.5.2 such that the driving clip 7.5 is led into a lateral mid position when the button 7 is urged towards the proximal end of the dose selector 8 by the clutch spring 13.

Under a torque applied on the dose selector 8, the inclined face of the conical tip 7.5.2 slides along the correspondingly inclined face of the proximal end of the recess pocket 8.1. Thus, the driving clip 7.5 partially translates against the spring force of the clutch spring 13 in a distal direction while the dose selector 8 rotates relative to the button 7 until the rotational play is exhausted. The spring force of the clutch spring 13 urges, as a restoring force, the driving clip 7.5 back into its lateral mid position such that the torque on the dose selector 8 is partially absorbed. Thereby, torque peaks along the drive train T are smoothened, such that rattling noises or tactile discontinuities are minimized.

Figure 19:
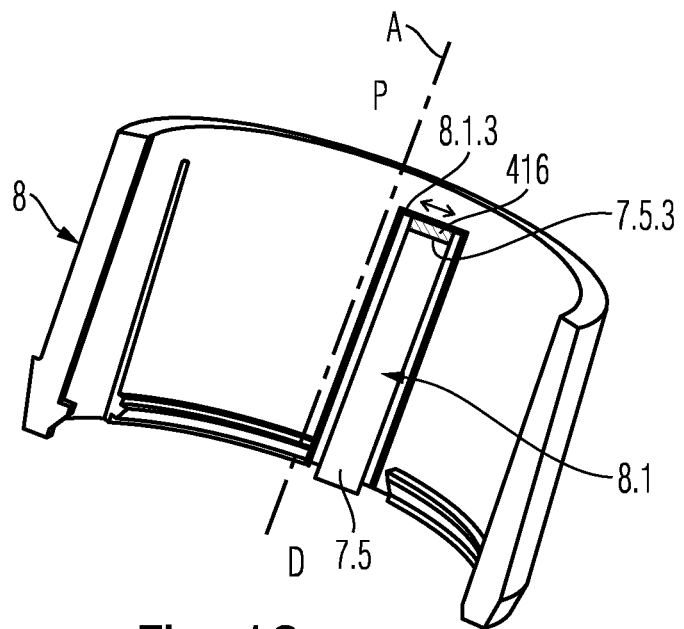

FIG. 19 shows a perspective view on a further embodiment of a driving clip 7.5 and a recess pocket 8.1. A driving clip 7.5 is formed as a post with a flat proximal front surface 7.5.3 perpendicular to the longitudinal axis A. The lateral, circumferential width of the pocket 8.1 exceeds the width of the clip 7.5, thereby allowing a rotational play between the button 7 and the dose selector 8. The front surface 8.1.3 at the proximal end of the recess pocket 8.1 is formed flat perpendicular to the longitudinal axis A. A frictional layer 416 with viscous friction characteristics is arranged in between the coplanar faces of the front surface 7.5.3 of the driving clip 7.5 and the front surface 8.1.3 of the recess pocket 8.1. The frictional layer 416 may be formed as a coating on either of the front surfaces 7.5.3, 8.1.3, for example by a two-component injection moulding as known from the state of the art. The button 7 is urged along the longitudinal axis A towards the proximal end of the dose selector 8 by the clutch spring 13, such that a friction force caused by the frictional layer 416 resists a relative, lateral translation of the driving clip 7.5 and the recess pocket 8.1. Thereby, the rotation of the dose selector 8 relative to the button 7 within the rotational play is dampened, such that rattling noises or tactile discontinuities are minimized.

Figure 20:
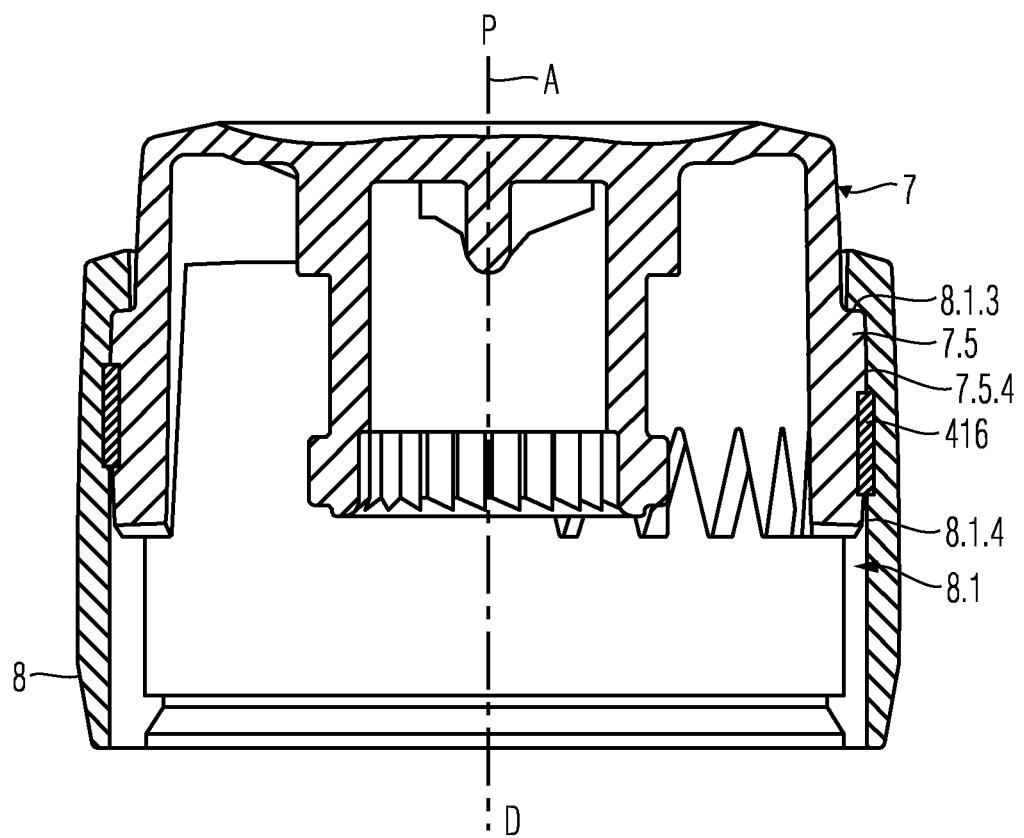
FIG. 20 is a schematic longitudinal section of a button and a dose selector.

FIG. 20 shows a longitudinal section of a further embodiment of a driving clip 7.5 and a recess pocket 8.1. The driving clip 7.5 provides a radially outwardly directed radial surface 7.5.4 that is preferably in all-over contact with the radially inwardly directed radial surface 8.1.4 of the pocket 8.1. The lateral or circumferential width of the pocket 8.1 exceeds the lateral or circumferential width of the driving clip 7.5 to enable a rotational play between the dose selector 8 and the button 7.

The contacting radial surfaces 7.5.4, 8.1.4 cause friction that resists a rotation of the dose selector 8 relative to the button 7 within the rotational play. Preferably, a driving clip 7.5 is formed with a radial excess width to increase the contact pressure between the contacting radial surfaces 7.5.4, 8.1.4. Preferably, on either of the contacting radial surfaces 7.5.4, 8.1.4, a frictional layer 416 with viscous friction characteristics is arranged. The frictional layer 416 may be formed as a coating on either of the radial surfaces 7.5.4, 8.1.4, for example by a two-component injection moulding as known from the state of the art. By friction along the frictional layer 416, the rotation of the dose selector 8 relative to the button 7 within the rotational play is dampened, such that rattling noises or tactile discontinuities are minimized.

Figure 21:
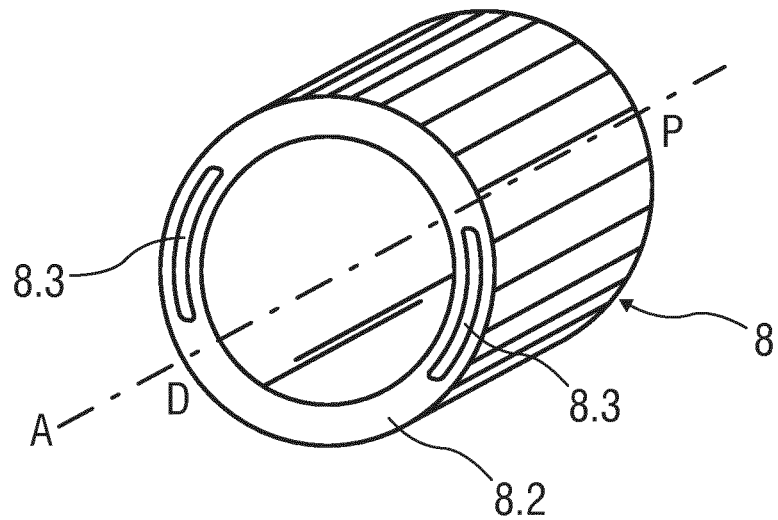
FIG. 21 is a schematic perspective view on a dose selector with a collar.

FIG. 21 shows a perspective view on an embodiment of a dose selector 8 formed as a dial grip. An inwardly protruding mounting collar 8.2 is formed on the proximal end P of the dose selector 8. As can be seen back in FIG. 4, the collar 8.2 engages an annular recess 2.1 formed into the proximal end P of the housing 2. The dose selector 8 according to this embodiment is made of a visco-elastical material, i.e. a material that comprises both viscosity, i.e. a strain rate depending on time, and elasticity, i.e. resistance against deformation and relaxation of such deformation.

Upon mounting, the distal end D of the dose selector 8 is led from the proximal end P of the housing 2 along the longitudinal axis A in a distal direction. Due to its elasticity, the diameter of the collar 8.2 widens until the collar 8.2 engages the annular recess 2.1 in its mounting position shown in FIG. 4.

In its mounting position, the collar 8.2 tightly fits the annular recess 2.1. In order to further tighten this fit, outer diameter of the annular recess 2.1 exceeds the inner diameter of the collar 8.2. Arching cut-outs 8.3 are formed into the collar 8.2. As the visco-elastical material is weakened along these cut-outs 8.3, the radial elasticity of the collar 8.2 is improved.

It is thus possible to mount the collar 8.2 radially preloaded around the annular recess 2.1 such that the viscoelastical material of the collar 8.2 visco-frictionally engages the housing 2. thereby increasing the frictional resistance against a rotation of the dose selector 8 relative to the housing 2. By such an increased friction, torque peaks along the drive train T that cause acoustic and tactile discontinuities, are reduced. As a further advantage, said increased frictional resistance adds to the holding force of the clutch element 12 that prevents the drive spring from unloading. Thus, unintended unloading of the drive spring 9 is prevented more reliably. As a further advantage, said increased frictional resistance dampens rattle noises that are caused by soft torsion elements and by positive-locking interfaces along the drive train T for charging or discharging the torsion drive spring 9. As yet another advantage, the torque exerted by the drive spring 9 on the drive sleeve 5 is not decreased by the friction between the dose selector 8 and the housing 2. Therefore, the expelling of the drug by the drive sleeve 5 driving the piston rod 4 is not compromised.

As a further advantage, due to the increased friction the resulting torque that is applied from the drive spring 9 onto a clutch element 12 is reduced. Thereby, the specification of the clutch element 12 can be relaxed. For example, a clutch element 12 comprising dialling clutch teeth can be designed to withstand less torque, thereby requiring less steep teeth profiles for the clutch teeth. As the teeth geometry is relaxed, the loudness of the dialling can be reduced.

Figure 22:
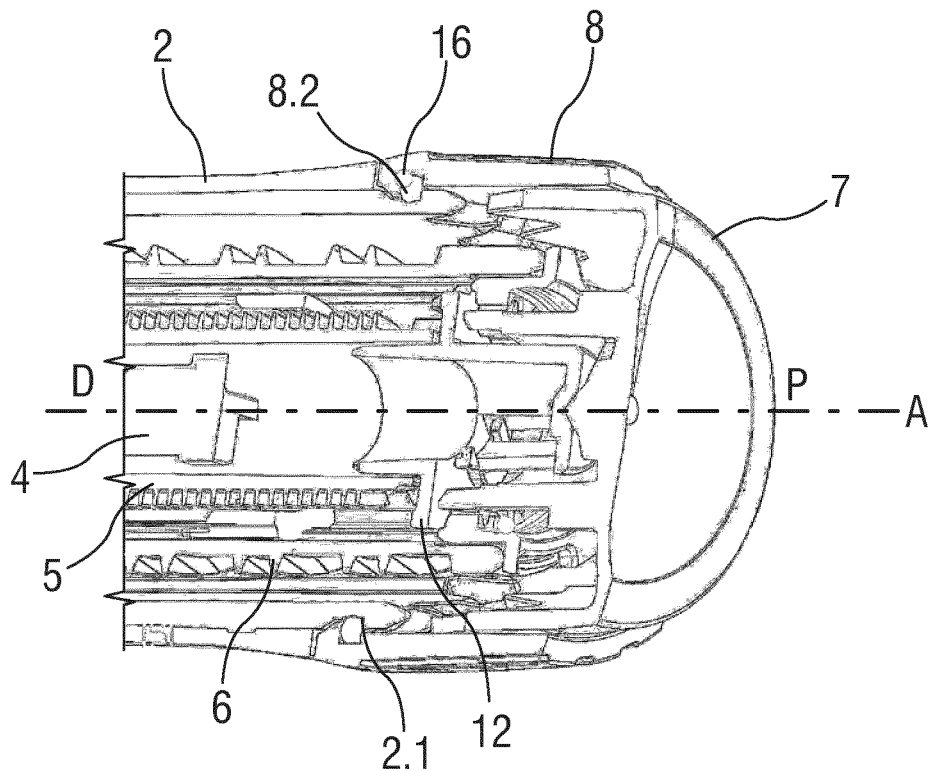
FIG. 22 is a schematic longitudinal section of a driving mechanism with an O-ring.

FIG. 22 shows a perspective view on an embodiment of a driving mechanism with an O-ring 16 similar to the embodiment shown in FIG. 4. This embodiment differs from the one shown in FIG. 4 in that the O-Ring 16 is arranged between the dose selector 8 and the housing 2. On the distal end of the dose selector 8 a radially inwardly protruding collar 8.2 is arranged. The collar 8.2 engages an annular recess 2.1 formed into the proximal end of the housing 2, thereby preventing the dose selector 8 from sliding in the proximal direction relative to the housing 2, as explained before with FIG. 21. In addition to the embodiment according to FIG. 22, an annular recess 8.4 is carved into the inner cylindrical surface of the dose selector 8 facing the proximal face of the collar 8.2. The annular recesses 2.1, 8.4 form a cavity that receives the O-ring 16. The O-ring 16 is formed of a visco-elastical material, e.g. of rubber, and is formed to tightly fill said cavity 2.1, 8.4. Thereby, the axial play between the housing 2 and the dose selector 8 is reduced or avoided.

As a further advantage, the O-ring 16 visco-frictionally resists the rotation of the dose selector 8 relative to the housing 2, thereby dampening torque peaks along the drive train t from the dose selector 8 towards the drive spring 9. By such an increased friction, torque peaks along the drive train T that cause acoustic and tactile discontinuities, are reduced. As a further advantage, said increased frictional resistance adds to the holding force of the clutch element 12 that prevents the drive spring from unloading. Thus, unintended unloading of the drive spring 9 is prevented more reliably. As a further advantage, said increased frictional resistance dampens rattle noises that are caused by soft torsion elements and by positive-locking interfaces along the drive train T for charging or discharging the torsion drive spring 9. As yet another advantage, the torque exerted by the drive spring 9 on the drive sleeve 5 is not decreased by the friction between the dose selector 8 and the housing 2. Therefore, the expelling of the drug by the drive sleeve 5 driving the piston rod 4 is not compromised.

Figure 23A:
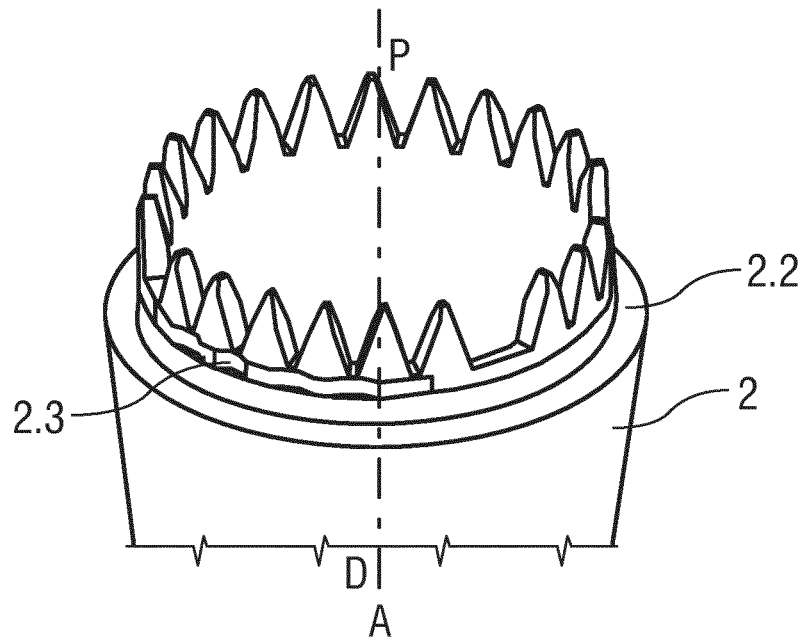
FIG. 23A is a schematic perspective view on a housing with radial detents and FIG. 23B is a schematic cross section through a housing with radial detents and a dose selector mounted on the housing.

FIG. 23A shows a perspective view on the proximal end P of an embodiment of a housing 2 being radially inwardly recessed in order to receive a dose selector 8. Upon mounting, the dose selector 8 is urged in a distal direction over the proximal end P of the housing 2 until it abuts the distal face of the radial recess 2.2. Along an outer circumference CO being an outer perimeter of the radial recess 2.2, four radial detents 2.3 are arranged that are radially inwardly worn into the radial recess 2.2.

Figure 23B:
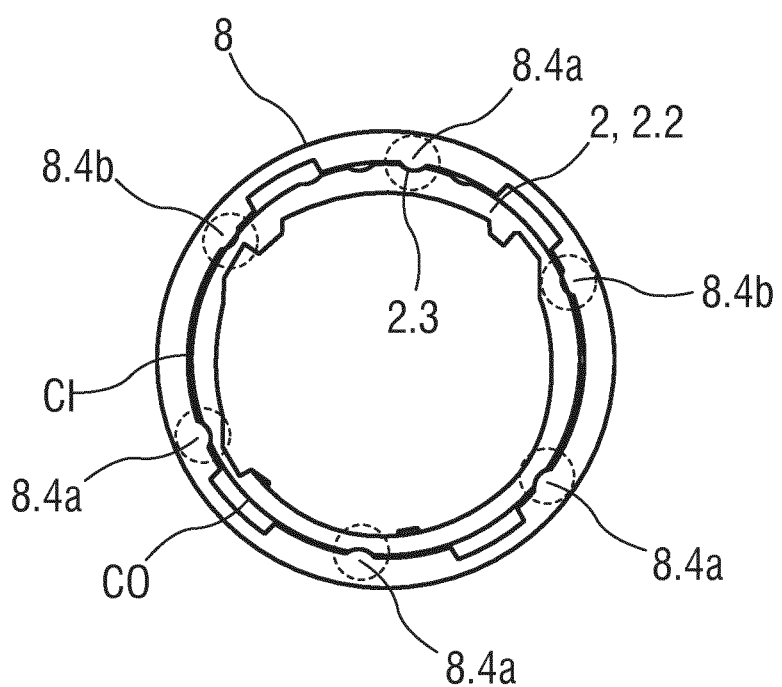

As can be seen in more detail in FIG. 23B, the radial detents 2.3 are trough-shaped along a cross-section through the housing 2. As can be further seen in FIG. 23B, the dose selector 8 provides six radially inwardly protruding pips 8.5*a*, 8.5*b* that are circumferentially equidistantly arranged along an inner circumference CI being a perimeter on the inner cylindrical surface of the dose selector 8. The four radial detents 2.3 are arranged such that in a first locked-in angular position of the dose selector 8 relative to the housing 2, four pips 8.5*a* are received in corresponding radial detents 2.3. The remaining two pips 8.5*b* are not received in radial detents 2.3 but abut the outer surface of the radial recess 2.2. The dose selector 8 or at least the pips 8.5*a*, 8.5*b* are made of a visco-elastical material.

The abutting pips 8.5*b* visco-frictionally resist a rotation of the dose selector 8 relative to the housing 2 and furthermore reduce or avoid a radial play between the dose selector 8 and the housing 2. The received pips 8.5*a* visco-elastically resist a rotation of the dose selector 8 out of its locked-in angular position. Upon turning the dose selector 8 by 60 degrees, four pips 8.5*a*, 8.5*b* will lock in in a further locked-in angular position again as they are received by radial detents 2.3.

Those skilled in the art will appreciate that arbitrary angular steps between locked-in angular positions can be reached by an appropriate number of circumferentially equidistantly spaced radial detents 2.3 and correspondingly arranged pips 8.5*a*, 8.5*b*. According to this embodiment, the locked-in angular positions are chosen such that they coincide with the angular positions of the ratchet 12.4 of the clutch element 12 corresponding to pre-dialled dosage steps as explained with FIG. 2.

As an advantage, the pips 8.5*a*, 8.5*b* visco-frictionally resists the rotation of the dose selector 8 relative to the housing 2 in between locked-in angular positions, thereby dampening torque peaks along the drive train t from the dose selector 8 towards the drive spring 9 when choosing a dosage. By such an increased friction, torque peaks along the drive train T that cause acoustic and tactile discontinuities, are reduced. As a further advantage, said increased frictional resistance dampens rattle noises that are caused by soft torsion elements and by positive-locking interfaces along the drive train T for charging or discharging the torsion drive spring 9. As yet another advantage, the torque exerted by the drive spring 9 on the drive sleeve 5 is not decreased by the friction between the user handle 8 and the housing 2. Therefore, the expelling of the drug by the drive sleeve 5 driving the piston rod 4 is not compromised.

As a further advantage, the torque resistance applied by the visco-elasticity of the received pips 8.5*a* in a locked-in angular position adds to the torque resistance effected by the ratchet 12.4. Thereby it is possible to relax the requirements regarding the ratchet 12.4 of the clutch 12. In particularity, it is possible to reduce the holding torque applied by the clutch 12 to hold the number sleeve 6 in one of a predetermined number of angular positions corresponding to discrete selectable dosages.

The application of the holding torque near the beginning of the drive train T for loading the drive spring 9, i.e. nearby the user handle 8, is advantageous in terms of a more precise tactile experience when selecting a dosage. On the other hand, the application of the holding torque near the end of the drive train T, i.e. at the clutch 12, is advantageous in terms of a more precise and reliable selection of the dosage itself, as tolerances along the drive train T from the user handle 8 to the clutch 12 do not compromise the precision of the selected dosage.

It is an advantage of this embodiment that by splitting the holding torque along the drive train T, i.e. application of one part of the holding torque by the visco-elastical and visco-frictional engagement of the pips 8.5*a*, 8.5*b* with the radial detents 2.3 in addition to application to another part of the holding torque by the ratchet 12.4, both the precision of the tactile experience and the precision of the set dosage can be improved.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 wind-up injection device
2 housing
2.1 annular recess
2.2 radial recess
2.3 radial detent
3 cartridge holder
4 piston rod
5 drive sleeve
5.1 second circumferential recess
5.2.1 proximal drive sleeve ring
5.2.2 distal drive sleeve ring
6 number sleeve, rotatable element
6.1 axial slot
7 button
7.1 outer button wall
7.2 inner button wall
7.3 button lid
7.4 guide pin
7.5 driving clip
7.5.1 clip arm
7.5.2 conical tip
7.5.3 front surface
7.5.4 radial surface
8 dose selector, user handle
8.1 pocket
8.1.1 guiding section
8.1.2 holding section
8.1.3 front surface
8.1.4 radial surface
8.2 collar
8.3 cut-out
8.4 annular recess
8.5a, 8.5b pip
9 drive spring
9.1 distal spring end
9.2 proximal spring end
10 cartridge
11 gauge element
12 clutch element
12.1 cylindrical clutch section
12.2 clutch plate
12.3 first circumferential recess
12.4 ratchet
12.5 clutch lid
12.6 blind hole
12.7 denting
12.8 resilient arm, dampening element
12.9 radial stop
12.10 resilient fork, dampening element
13 clutch spring, spring
14 bearing
15 stopper
16 O-ring, dampening element
116 distance ring, dampening element
116.1 protrusion
116.2 radial recess
216 tubular dampening element
216.1 tapered end
216.2 expanded end
316 friction ring, dampening element
416 frictional layer, dampening element
A longitudinal axis
CI inner circumference
CO outer circumference
D distal end T drive train
P proximal end
PI positive interface

The invention claimed is:

1. A drive train for a wind-up injection device for injecting a liquid drug, the drive train comprising:
a torsional energy storage adapted to be loaded or unloaded by a rotatable element;
a rotatable user handle;
a rotationally driveable expelling mechanism adapted to expel the liquid drug;
a clutch element coupled with the torsional energy storage via the rotatable element and comprising a ratchet for maintaining the rotatable element at one of a number of discrete angular positions against a torque of the torsional energy storage,
wherein the clutch element is adapted to transmit a torque from the user handle via the rotatable element to the torsional energy storage or alternatively from the torsional energy storage via the rotatable element to the expelling mechanism,
wherein the ratchet is switchable from one position to an adjacent position by the torque transmitted from the user handle to the torsional energy storage; and
a dampening element adapted to dampen torque peaks, and comprising a visco-elastic dampening element adapted to elastically transmit a torque, and/or a visco-frictional dampening element adapted to frictionally resist a rotation; and
wherein the dampening element comprises the visco-elastic dampening element, and the visco-elastic dampening element is arranged in a radial direction between the user handle and the ratchet, wherein the user handle surrounds the visco-elastic dampening element and the ratchet, or
wherein the torsional energy storage comprises a housing, wherein the dampening element comprises the visco-frictional dampening element, and the visco-frictional dampening element is formed as a bushing that is torque proof coupled with the user handle and that is longitudinally coupled with the user handle and with the housing and that at least partially visco-frictionally directly engages an outer surface of the housing, wherein the bushing is formed as a radially inwardly protruding collar for the user handle in the direction of the housing, the collar being received in an annular recess along an outer circumference of the housing.

2. The drive train according to claim 1, wherein the dampening element comprises the visco-frictional dampening element, and the visco-frictional dampening element is arranged between two elements of the drive train that are rotatable relative to each other.

3. The drive train according to claim 2, wherein the visco-frictional dampening element comprises at least one surface of elastic rubber adapted to slide along a contact surface of a particular element of the drive train when rotated relatively to that particular element.

4. The drive train according to claim 1,
wherein the housing includes a longitudinal axis extending from a proximal towards a distal end and a torsional drive spring with a distal spring end non-rotatably engaged to the housing and with a proximal spring end torsionally tensible around the longitudinal axis relative to the housing,
wherein the expelling mechanism comprises a drive sleeve arranged within the housing and rotatable around the longitudinal axis, wherein rotation of the drive sleeve relative to the housing is configured to cause a piston rod to translate relative to the housing, and
wherein the clutch element comprises a cylindrical clutch section and is adapted to releasably non-rotatably couple the proximal spring end of the drive spring with the drive sleeve.

5. The drive train according to claim 1, wherein the clutch element is coupled to the rotatable element by a circumferentially resilient visco-elastic dampening element,
wherein the rotatable element is formed as a tubular number sleeve adapted to at least partially receive the clutch element, and
wherein the circumferentially resilient visco-elastic dampening element radially protrudes from the clutch element and a radially outward end of the circumferentially resilient visco-elastic dampening element is received circumferentially non-slippably in an axial slot that is arranged on an inner surface of the tubular number sleeve coaxially to a longitudinal axis of the housing of the torsional energy storage.

6. The drive train according to claim 1, wherein the housing of the torsional energy storage comprises a longitudinal axis,
wherein the user handle provides at least one pocket and is releasably non-rotatably coupled with the rotatable element by a button providing at least one driving clip, and
wherein a driving clip is led axially displaceable along a longitudinal axis in a corresponding pocket and is wedged non-rotatably when urged in a proximal direction relative to the corresponding pocket.

7. The drive train according to claim 1, wherein the housing of the torsional energy storage comprises a longitudinal axis,
wherein the user handle provides at least one pocket and is releasably non-rotatably coupled with the rotatable element by a button providing at least one driving clip, wherein a driving clip is led axially displaceable along the longitudinal axis with a rotational play in a corresponding pocket and wherein the driving clip is resiliently forced into a circumferential center position.

8. A wind-up injection device for injecting a liquid drug, the wind-up injection device comprising:
the liquid drug; and
a drive train comprising
a torsional energy storage adapted to be loaded or unloaded by a rotatable element,
a rotatable user handle,
a rotationally driveable expelling mechanism adapted to expel the liquid drug, and
a clutch element coupled with the torsional energy storage via the rotatable element and comprising a ratchet for maintaining the rotatable element at one of a number of discrete angular positions against a torque of the torsional energy storage,
wherein the clutch element is adapted to transmit a torque from the user handle via the rotatable element to the torsional energy storage or alternatively from the torsional energy storage via the rotatable element to the expelling mechanism,
wherein the ratchet is switchable from one position to an adjacent position by the torque transmitted from the user handle to the torsional energy storage, and
a dampening element adapted to dampen torque peaks, and comprising a visco-elastic dampening element adapted to elastically transmit a torque, and/or a visco-frictional dampening element adapted to frictionally resist a rotation, and wherein the dampening element comprises the visco-elastic dampening element, and the visco-elastic dampening element is arranged in a radial direction between the user handle and the ratchet, wherein the user handle surrounds the visco-elastic dampening element and the ratchet, or wherein the torsional energy storage comprises a housing, wherein the dampening element comprises the visco-frictional dampening element, and the visco-frictional dampening element is formed as a bushing that is torque proof coupled with the user handle and that is longitudinally coupled with the user handle and with the housing and that at least partially visco-frictionally directly engages an outer surface of the housing, wherein the bushing is formed as a radially inwardly protruding collar for the user handle in the direction of the housing, the collar being received in an annular recess along an outer circumference of the housing.

\* \* \* \* \*